(12) United States Patent
 Willett

(10) Patent No.: US 9,408,934 B2
(45) Date of Patent: Aug. 9, 2016

(54) COMPOSITIONS AND METHODS FOR IMPROVING TOUGHNESS OF IRRADIATED STERILIZED BONE ALLOGRAFTS

(71) Applicant: Sinai Health System, Toronto (CA)

(72) Inventor: Thomas Willett, Whitby (CA)

(73) Assignee: Sinai Health System, Toronto (CA)

(*) Notice: Subject to any disclaimer, the term of this patent is extended or adjusted under 35 U.S.C. 154(b) by 137 days.

(21) Appl. No.: 14/055,365

(22) Filed: Oct. 16, 2013

(65) Prior Publication Data
US 2014/0112825 A1    Apr. 24, 2014

Related U.S. Application Data

(60) Provisional application No. 61/717,321, filed on Oct. 23, 2012.

(51) Int. Cl.
*A61L 2/00* (2006.01)
*A61L 9/00* (2006.01)

(52) U.S. Cl.
CPC .... *A61L 9/00* (2013.01); *A61L 2/00* (2013.01)

(58) Field of Classification Search
CPC .............................. A61L 2/0035; A61L 2/00
USPC ............................................................ 422/22
See application file for complete search history.

(56) References Cited

U.S. PATENT DOCUMENTS 6,682,695 B2 * 1/2004 MacPhee et al. ............. 422/22
6,739,112 B1 * 5/2004 Marino ........................... 53/431

OTHER PUBLICATIONS

Akkus O and Belaney RM. Sterilization by gamma radiation impairs the tensile fatigue life of cortical bone by two orders of magnitude. J Orthop Res, Sep. 2005; 23(5):1054-1058.
Akkus O and Rimnac CM. Fracture resistance of gamma radiation sterilized cortical bone allografts. J Orthop Res, Sep. 2001; 19(5):927-934.
Akkus O et al. Free radical scavenging alleviates the biomechanical impairment of gamma radiation sterilized bone tissue. J Orthop Res, Jul. 2005; 23(4):838-845.
An Y and Friedman RJ. Animal Models of Bone Defect Repair. In: An Y, Friedman RJ, editors. Animal Models in Orthopaedic Research. Boca Raton: CRC Press, 1999. p. 241-260.
Bank RA et al. A simplified measurement of degraded collagen in tissues: application in healthy, fibrillated and osteoarthritic cartilage. Matrix Biol. Nov. 1997; 16:233-43.
Bank RA et al. Sensitive fluorimetric quantitation of pyridinium and pentosidine crosslinks in biological samples in a single high performance liquid chromatographic run. Journal of Chromatography: B, Biomedical Sciences and Applications. Dec. 5, 1997; 703(1-2):37-44.
Barth HD et al. Characterization of the effects of x-ray irradiation on the hierarchical structure and mechanical properties of human cortical bone. Biomaterials, Dec. 2011, 32(34): 8892-904.

(Continued)

*Primary Examiner* — Sean E Conley
(74) *Attorney, Agent, or Firm* — Howson & Howson LLP

(57) ABSTRACT

The present invention relates to compositions, methods, kits and systems employing irradiation activated agents to improve or increase or prevent loss of toughness, work-to-fracture, post-yield toughness, fracture toughness and/or fatigue strength of a bone allograft on exposure to radiation. The irradiation activated agent can be an agent that increases crosslinking of collagen in bone during irradiation, for example ribose, 2-hydroxytetrahydropyran or ascorbate.

3 Claims, 23 Drawing Sheets

(56) References Cited

OTHER PUBLICATIONS

Callister WD. Diffusion. In: Callister WD, editor. Materials Science and Engineering: An Introduction. Toronto: John Whiley and Sons, 1994. p. 89.
Haimi S et al. The effect of chemical cleansing procedures combined with peracetic acid-ethanol sterilization on biomechanical properties of cortical bone. Biologicals, Mar. 2008; 36:99-104.
Hertzberg, RW. Deformation and Fracture Mechanics of Engineering Materials. Fourth ed. New Jersey: John Wiley and Sons, 1995.
Kattaya SA et al. Radioprotectant and radiosensitizer effects on sterility of gamma-irradiated bone. Clinical Orthopaedics and Related Research. Aug. 2008;466(8):1796-803.
Lakey JR et al. Demand for human allograft tissue in Canada. Cell Tissue Bank, Mar. 2007; 8(1):31-42.
Landrigan MD et al. Contrast-enhanced microcomputed tomography of fatigue microdamage accumulation in human cortical bone. Bone, Mar. 1, 2011;48(3):443-50.
Leng H et al. Micro-computed tomography of fatigue microdamage in cortical bone using a barium sulfate contrast agent. J Mechanical Behavior of Biomedical Materials, Jan. 2008;1(1):68-75.
Levine RL, et al. Determination of carbonyl groups in oxidized proteins. Methods Mol Biol 2000; 99:15.
Lietman SA et al. Complications of irradiated allografts in orthopaedic tumor surgery. Clin Orthop Relat Res, Jun. 2000;(375):214-217.
Mankin HJ et al. Massive Allograft Transplantation Following Tumor Resection. In: Friedlaender GE, Mankin HJ, Goldberg VM, editors. Bone Grafts and Bone Graft Substitutes. Rosemont, IL: American Academy of Orthopaedic Surgeons, 2006: 39-47.
Materials ASftTo. Standard test method for measurement of fracture toughness. ASTM, 2009.
Miles CA et al. Differential scanning calorimetric studies of superficial digital flexor tendon degeneration in the horse. Equine Vet.J. Jul. 1994;26(4):291-6.
Miles CA et al. The increase in denaturation temperature following cross-linking of collagen is caused by dehydration of the fibres. J.Mol.Biol. Feb. 18, 2005;346(2):551-6. Epub Dec. 23, 2004.
Miles CA. Differential scanning calorimetry (DSC): protein structure probe useful For the study of damaged tendons. Equine Vet.J. Jul. 1994;26:255.
Miles CA. Kinetics of collagen denaturation in mammalian lens capsules studied by differential scanning calorimetry. Int.J.Biol. Macromol. Oct. 1993;15(5):265-71.
Mitchell EJ et al. The effect of gamma radiation sterilization on the fatigue crack propagation resistance of human cortical bone. J Bone Joint Surg Am, Dec. 2004; 86-A(12):2648-2657.
Mroz T et al. Musculoskeletal allograft risks and recalls in the United States. J Am Acad Orthop Surg, Oct. 2008; 16(10):559-565.
Musculoskeletal Allograft Tissue Safety. New Orleans: American Academy of Orthopaedic Surgeons, 2010.
Nalla RK et al. Mechanistic fracture criteria for the failure of human cortical bone. Nat.Mater. Mar. 2003;2(3):164-8.
Nguyen H et al. Sterilization of allograft bone: effects of gamma irradiation on allograft biology and biomechanics. Cell Tissue Bank, 2007;8(2):93-105. Epub Oct. 25, 2006.
Standard Test Methods for Linear-Elastic Plane-Strain Fracture Toughness KIC of Metallic Materials, ASTM 399-09, 2009.
Thompson RC, Jr. et al. Fractures in large-segment allografts. Clin Orthop Relat Res, Jan. 2000; (370):227-235.
Willett et al, γ-Irradiation sterilizedbonestrengthenedand toughened byribosepre-treatment, J. Mechanical Behavior of Biomedical Materials, 44:147-55 (Jan. 2015).
Willett TL et al. Increased proteolysis of collagen in an in vitro tensile overload tendon model. Ann.Biomedical Engineering, Nov. 2007;35(11):1961-72. Epub Sep. 1, 2007.
Willett, T. L. et al (2010). Changes in collagen with aging maintain molecular stability after overload: Evidence from an in vitro tendon model. Journal of Biomechanical Engineering, Mar. 2010, 132(3):031002.
Willett, T. L. et al. In vitro non-enzymatic ribation reduces post-yield strain.accommodation in cortical bone. Bone, Feb. 2013;52(2):611-22. doi: 10.1016/j.bone.2012.11.014. Epub Nov. 22, 2012.
Willett, T. L. et al. Mechanical overload decreases the thermal stability of collagen in an in vitro tensile overload tendon model. Journal of Orthopaedic Research, Dec. 2008, 26(12), 1605-1610.
Wise, L. M. et al. The use of fractography to supplement analysis of bone mechanical properties in different strains of mice. Bone, Oct. 2007;41(4):620-30. Epub Jun. 29, 2007.
Wynnyckyj C et al. Changes in bone fatigue resistance due to collagen degradation. J.Orthop.Res. Feb. 2011;29(2):197-203. doi: 10.1002/jor.21228. Epub Aug. 27, 2010.
Wynnyckyj, C. et al. Fracture surface analysis to understand the failure mechanisms of collagen degraded bone. Journal of Bone and Mineral Metabolism,May 2011, 29(3), 359-368.
Yan J et al. Application of fracture mechanics to failure in manatee rib bone. J Biomech Eng, Jun. 2006; 128:281-9.
Yan J et al. How tough is bone? Application of elastic-plastic fracture mechanics to bone. Bone, Feb. 2007; 40(2):479-84.
Yan, J. et al. Fracture toughness of manatee rib and bovine femur using a chevron-notched beam test. Journal of Biomechanics, Apr. 19, 2005, 39(6):1066-1074.
Yang, Q. D. et al. Re-evaluating the toughness of human cortical bone. Bone, Jun. 2006;38(6):878-87. Epub Dec. 9, 2005.
Zhu, X. & Joyce, J. A. Review of fracture toughness (G, K, J, CTOD, CTOA) testing and standardization. Engineering Fracture Mechanics, May 2012, 85:1-46.
Zimmermann EA et al. Age-related changes in the plasticity and toughness of human cortical bone at multiple length scales. Proc Natl Acad Sci USA, Aug. 30, 2011;108(35):14416-21.
Zioupos P et al. The role of collagen in the declining mechanical properties of aging human cortical bone. J Biomed Mater Res, May 1999;45(2):108-16.

* cited by examiner

Figure 5
A
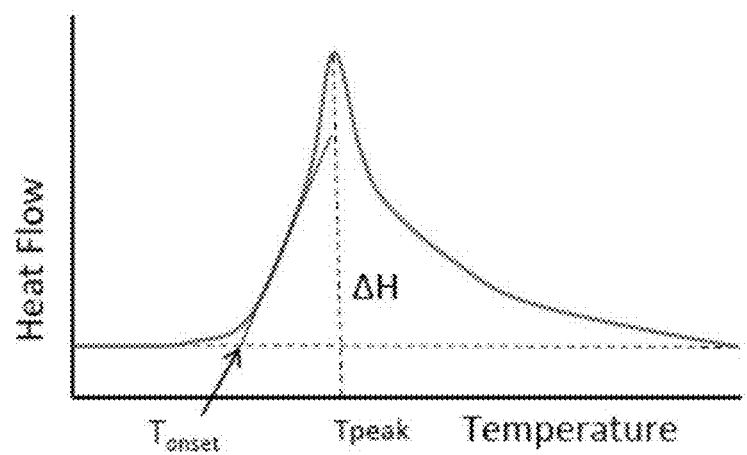
B
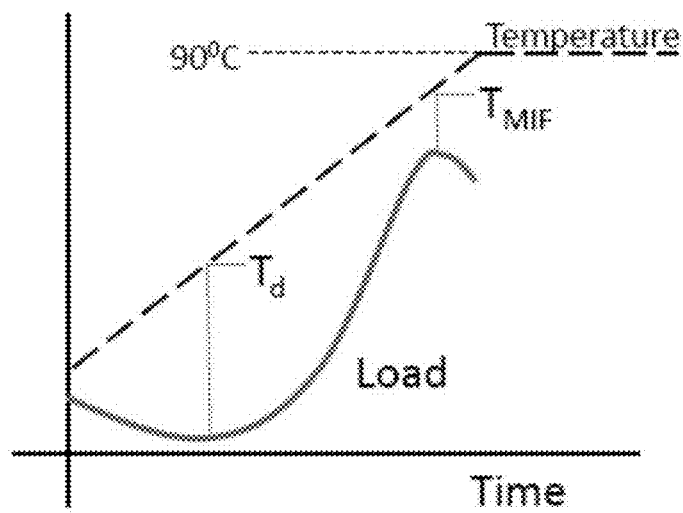

Figure 10
A
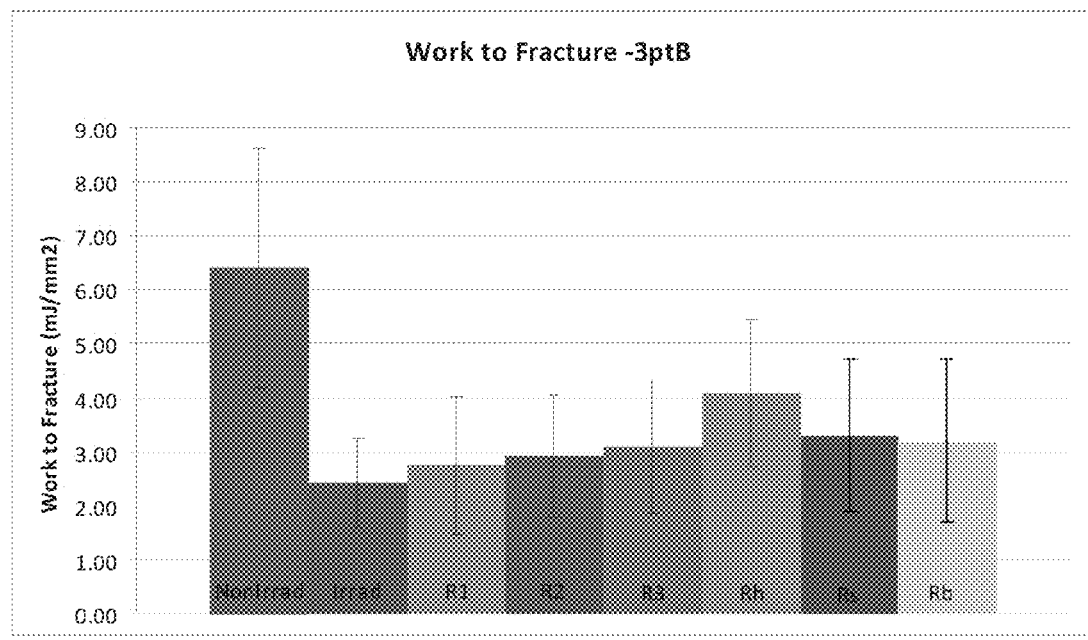
B
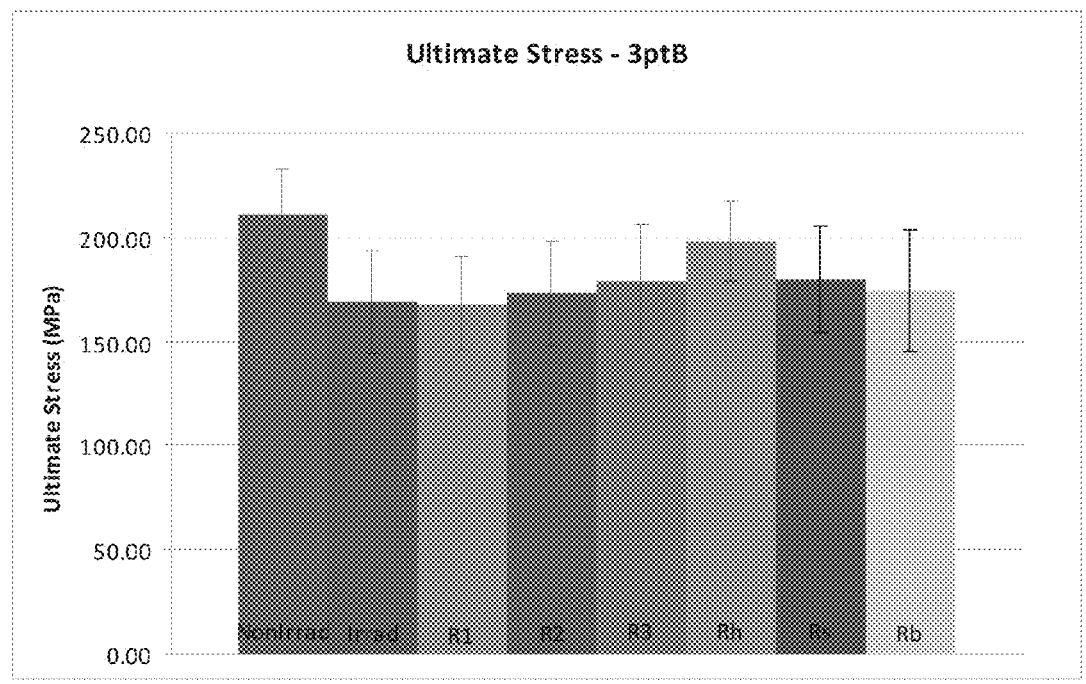

Figure 11
A
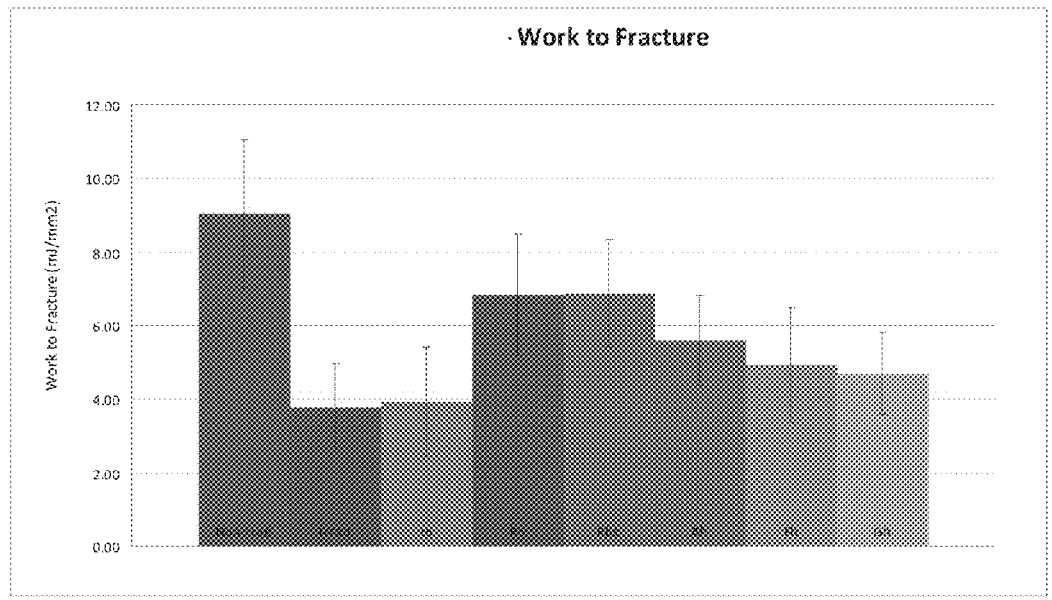
B
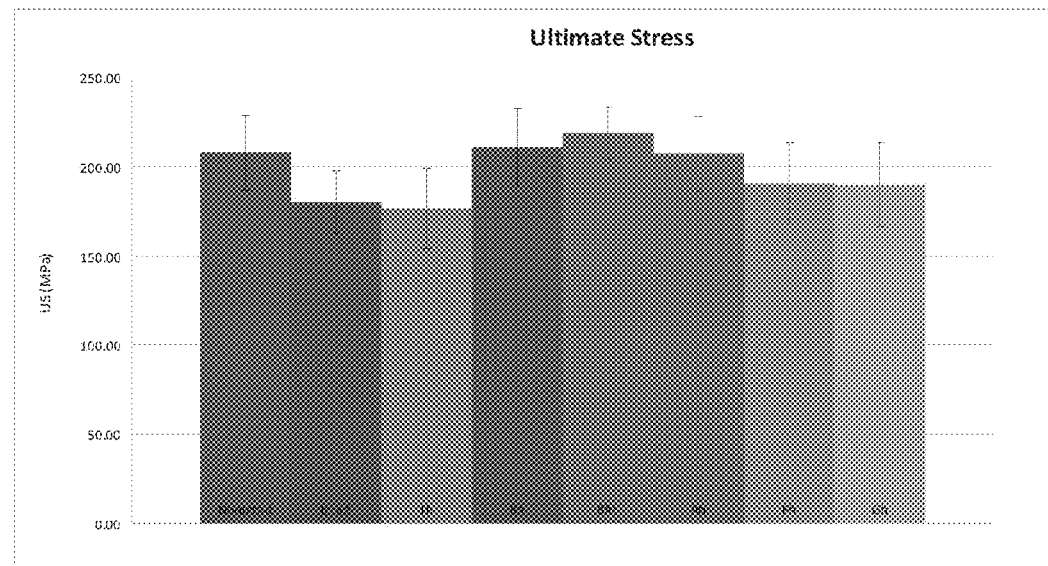

C.

Figure 12
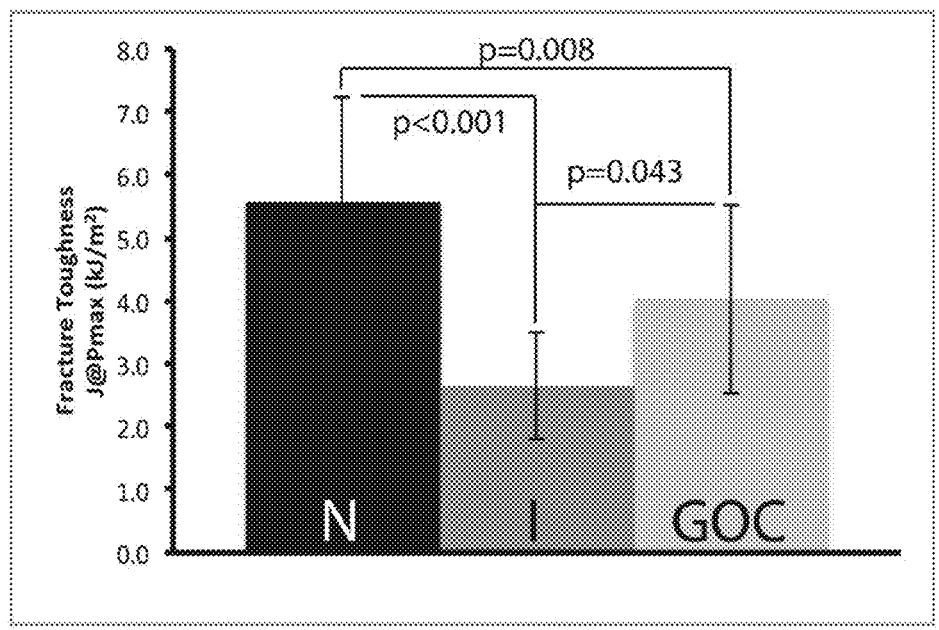
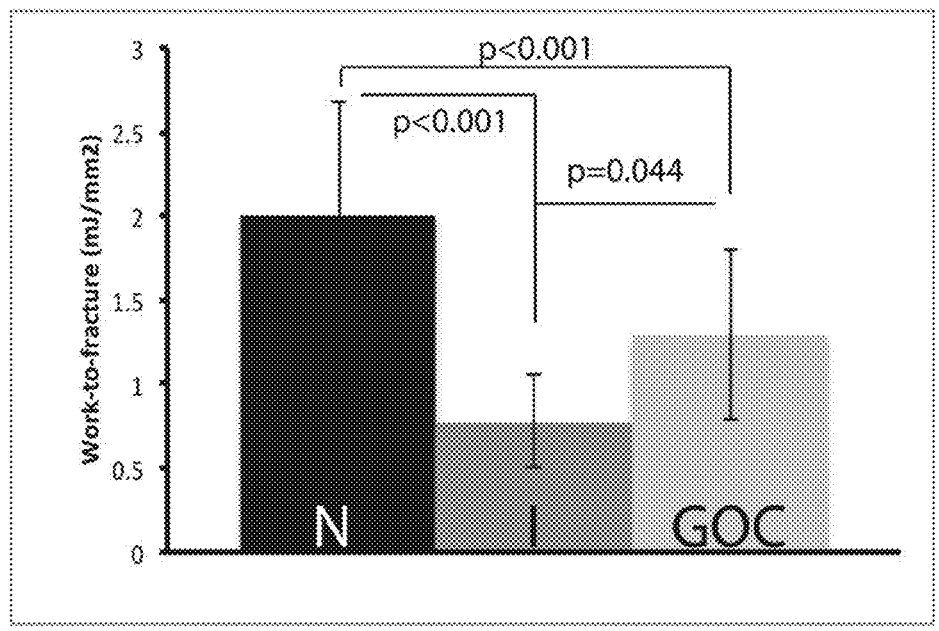

Figure 18
a
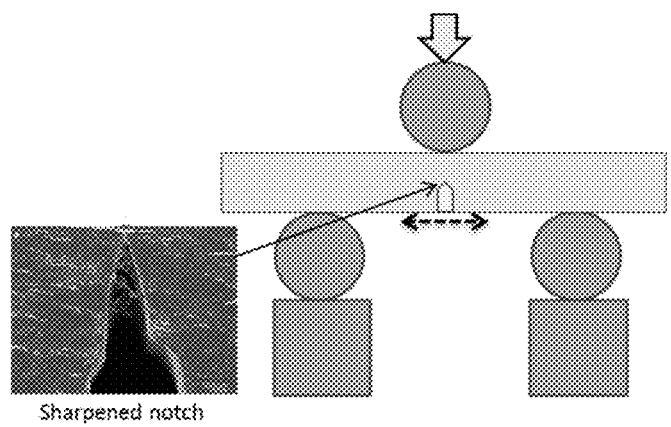
Sharpened notch
b
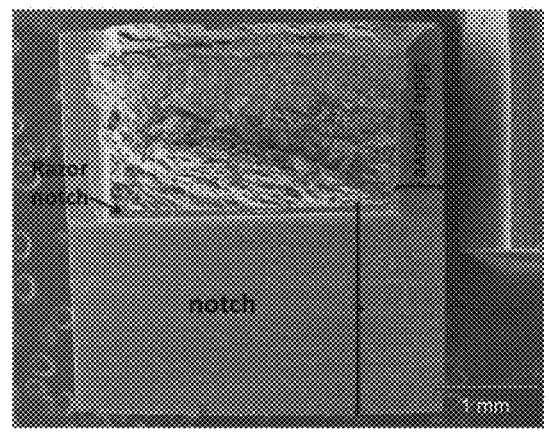

Figure 19
a
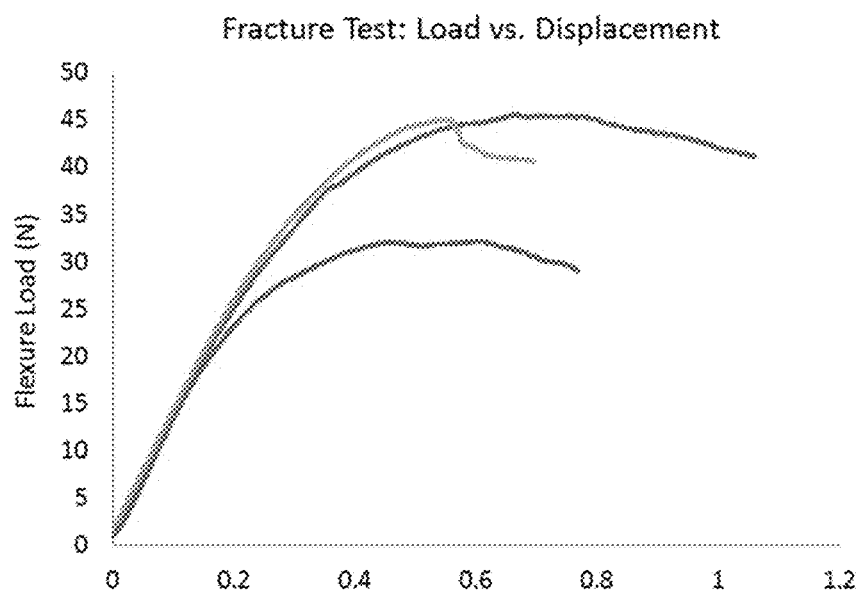
b
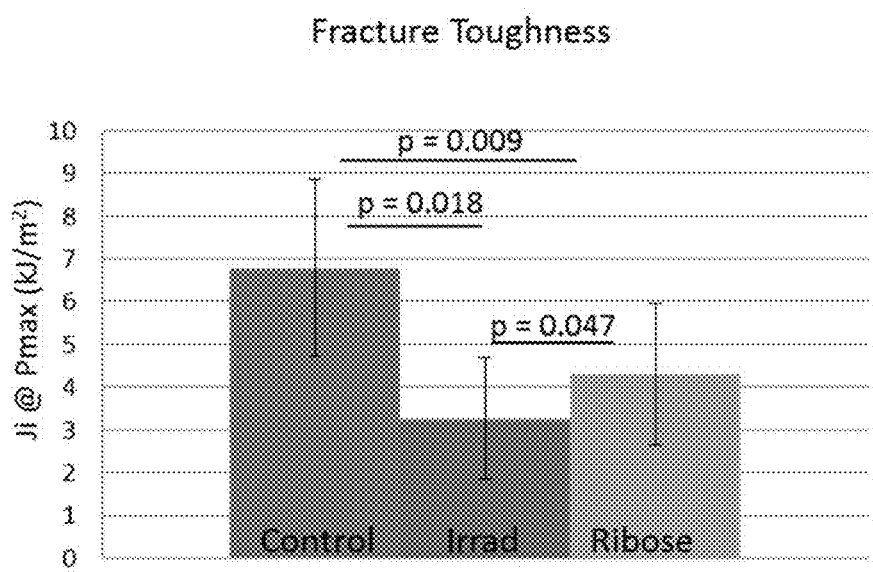

US 9,408,934 B2

COMPOSITIONS AND METHODS FOR IMPROVING TOUGHNESS OF IRRADIATED STERILIZED BONE ALLOGRAFTS

FIELD OF THE INVENTION

The present invention relates to compositions, methods, kits and systems for improving, or preventing or minimizing loss of, toughness, work-to-fracture, fracture toughness and/or fatigue strength of bone allografts on exposure to radiation.

BACKGROUND OF THE INVENTION

Musculoskeletal allografts produced by tissue banks from human donor tissues are used in a variety of orthopedic reconstructive surgeries. Over 1.5 million musculoskeletal allografts are used in the United States each year and this count is increasing steadily (1). Annual demand specifically for large structural cortical bone allografts in Canada is estimated at 16,000 grafts per year (2). An extrapolated estimate for the US is 160,000-320,000 per year (3). Large bone allografts are effectively devitalized bone-based implants which do not repair like living bone or autografts. Therefore, a large structural bone allograft must be able to fulfill its role for the long-term while resisting approximately a million loading cycles a year. The primary concern is donor-to-patient disease transmission. Terminal sterilization by γ-irradiation is used to sterilize allografts, eliminating bacteria, fungi and viruses and therefore greatly lowering infection risk (4).

γ-irradiation causes significant degradation of the mechanical performance of bone. Fracture rates for non-irradiated structural bone allografts range from 18% (5;6) to 42% (>26 months post implantation) (7). Irradiated structural allografts fracture at twice the rate of fresh allografts (6). Irradiation results in a safer product in terms of risk of infection but at the expense of graft quality and a heightened risk of fracture and revision surgery. An effective sterilization method which uses irradiation but maintains mechanical performance is required.

Bone is a biological composite tissue made of a stiff and brittle mineral phase toughened by collagen. The collagenous phase inhibits crack initiation and propagation. Irradiation of bone collagen results in highly fractured peptide chains and loss of native molecular structure (8). These changes result in severely reduced fracture toughness (9;10) and fatigue life (8;11). Fracture surfaces from irradiated bone (36 kGy on dry ice) are relatively flat and missing the fiber pullout/bridging and tortuous crack diversions typically seen in native bone (8;10;11), indicating a more brittle failure mode and correlating with highly fractured collagen content. Irradiation reduces toughness in tension by 86.4% and reduces low stress fatigue life to $1/10^{th}$ of normal and high stress fatigue life to $1/200^{th}$ of normal (11).

SUMMARY OF THE INVENTION

Applicant has found that the inclusion of an irradiation activated agent during irradiation of a bone allograft increases or restores the connectivity of the collagenous phase of the irradiated bone.

In an aspect, the present invention relates to a composition for treating a bone allograft exposed to radiation comprising an effective amount of an irradiation activated agent to improve, or prevent or minimize loss of, one or more of toughness, post-yield toughness, work-to-fracture, fracture toughness and fatigue strength on exposure of the bone allograft to radiation.

In another aspect, the invention relates to a method for processing a bone allograft comprising contacting the bone allograft with a composition effective to improve, restore, protect, or prevent or minimize loss of one or more of toughness, post-yield toughness, work-to-fracture, fracture toughness and/or fatigue strength on exposure of the bone allograft to radiation.

In another aspect, the invention relates to a method for processing a bone allograft comprising contacting the bone allograft with an effective amount of an irradiation activated agent to improve, restore, protect or prevent or minimize loss of one or more of toughness, post-yield toughness, work-to-fracture, fracture toughness and/or fatigue strength on exposure of the bone allograft to radiation.

In another aspect, the invention relates to a method for processing a bone allograft comprising contacting the bone allograft with an effective amount of an irradiation activated agent to restore or protect one or more of toughness, post-yield toughness, work-to-fracture, fracture toughness and/or fatigue strength otherwise lost to irradiation.

In another aspect, the invention relates to a method for processing a bone allograft comprising irradiating the bone allograft in the presence of an effective amount of an irradiation activated agent to improve, increase, restore, protect or prevent or minimize loss of toughness, post-yield toughness, work-to-fracture, fracture toughness and/or fatigue strength on exposure of the bone allograft to radiation. The method may additionally comprise removing lipids from the bone allograft. The method may additionally comprise inactivating the agent following radiation.

In another aspect, the invention relates to a method for processing a bone allograft comprising (a) treating the bone allograft with an effective amount of an irradiation activated agent to improve, increase, restore, protect or prevent or minimize loss of toughness, post-yield toughness, work-to-fracture, fracture toughness and/or fatigue strength on exposure of the bone allograft to radiation; and (b) irradiating the bone allograft. The method may additionally comprise removing lipids from the bone allograft. The method may additionally comprise inactivating the agent following radiation.

In another aspect, the invention relates to a method for processing a bone allograft comprising (a) treating the bone allograft with an effective amount of an irradiation activated agent to improve, restore, protect or prevent or minimize loss of toughness, post-yield toughness, work-to-fracture, fracture toughness and/or fatigue strength on exposure of the bone allograft to radiation; (b) irradiating the bone allograft, and (c) inactivating the agent. The method may additionally comprise removing lipids from the bone allograft. In an aspect the agent is inactivated by lyophilization or deep-freezing.

In another aspect, the invention relates to a method for increasing the toughness, work-to-fracture, fracture toughness and/or fatigue strength of irradiated bone allografts comprising treating the bone allografts with an irradiation activated agent prior to or during irradiation.

In another aspect, the invention relates to a method of preventing or minimizing loss of toughness, work-to-fracture, fracture toughness and/or fatigue strength in irradiated bone allografts comprising treating the bone allografts with an irradiation activated agent prior to or during irradiation.

In another aspect, the invention relates to a method of restoring or protecting one or more of toughness, post-yield toughness, work-to-fracture, fracture toughness and/or fatigue strength otherwise lost to irradiation in irradiated bone allografts comprising treating the bone allografts with an irradiation activated agent prior to or during irradiation.

The invention also provides a kit for treating a bone allograft comprising an irradiation activated agent to improve, increase, restore, protect, or prevent or minimize loss of, one or more of toughness, work-to-fracture, fracture toughness and fatigue strength on exposure of the bone allograft to radiation, and optionally a container.

The invention provides a system for packaging a bone allograft to be exposed to radiation which comprises a container having an effective amount of an irradiation activated agent to improve, increase, restore, protect or prevent or minimize loss of, toughness, work-to-fracture, fracture toughness and/or fatigue strength on exposure of the bone allograft to radiation.

In an aspect, a method of providing a bone allograft for use in a medical procedure is contemplated comprising introducing a bone allograft in a container having disposed therein a composition comprising an irradiation activated agent, wherein the irradiation activated agent is in an amount effective to improve, increase, restore, protect, or prevent or minimize loss of, toughness, work-to-fracture, fracture toughness and/or fatigue strength on exposure of the bone allograft to radiation. In an embodiment, the composition is introduced into the container prior to sealing the container and exposure to radiation. In another embodiment, the container comprises a self-sealing valve and the composition is introduced into the container through the self-sealing valve after the container is sealed. In a particular embodiment, a needle is employed to inject the composition through the self-sealing valve. In another embodiment, the container is primarily comprised of glass, plastic or metal foil, preferably plastic.

In an aspect the invention contemplates a system for treating a bone allograft prior to exposure to radiation comprising a container having disposed therein a composition comprising an irradiation activated agent, and the bone allograft sealed within the container, wherein the bone allograft is in contact with the composition under suitable conditions to substantially improve, increase, restore, protect or prevent or minimize loss of, toughness, work-to-fracture, fracture toughness and/or fatigue strength of the bone allograft on exposure to radiation. In an embodiment, the container has a self-sealing valve and the composition is introduced into the container through the self-sealing valve. In a particular embodiment, the system comprises a needle for injecting the composition through the self-sealing valve. In another embodiment the container comprises an outer impermeable layer, an inner layer for receiving a solution comprising a solute and the irradiation activated agent and a sealable opening, wherein the inner layer is porous to the solute and optionally the irradiation activated agent.

These and other aspects of the present invention will become evident upon reference to the following detailed description and attached drawings.

DESCRIPTION OF THE DRAWINGS

The invention will be better understood with reference to the drawings in which:

FIG. 5 are graphs illustrating results of (A) differential scanning calorimetry (DSC) and (B) hydrothermal isometric tension (HIT) studies. $T_{onset}$=onset of collagen denaturation. $\Delta H$=heat of denaturation. $T_d$=denaturation temperature. MIF=maximum isometric force. $T_{mif}$=temperature at maximum isometric force.

FIG. 12 shows (A) fracture toughness and (B) work-to-fracture of irradiated bovine cortical bone from the tibial diaphysis pre-treated with 1.8M ribose at 60° C. for 24 hours.

FIG. 18a is a schematic representation of the testing set-up for a single-edge notched beam fracture. The ~2 mm notch shown is cut with a diamond wire saw (diameter=300 μm) and sharpened by hand with a razor blade. FIG. 18b is an SEM image of a fractured sample, looking at the fracture surface.

FIG. 19a is an example of the load vs displacement curves for one matched set of single-edged notched beams tested in three-point bending. FIG. 19b is a graph representing the average J-integral values for each group with p-values for comparisons between groups. The J-integral was evaluated using the maximum load and the crack length at instability.

DETAILED DESCRIPTION OF PREFERRED EMBODIMENTS OF THE INVENTION

Figure 1:
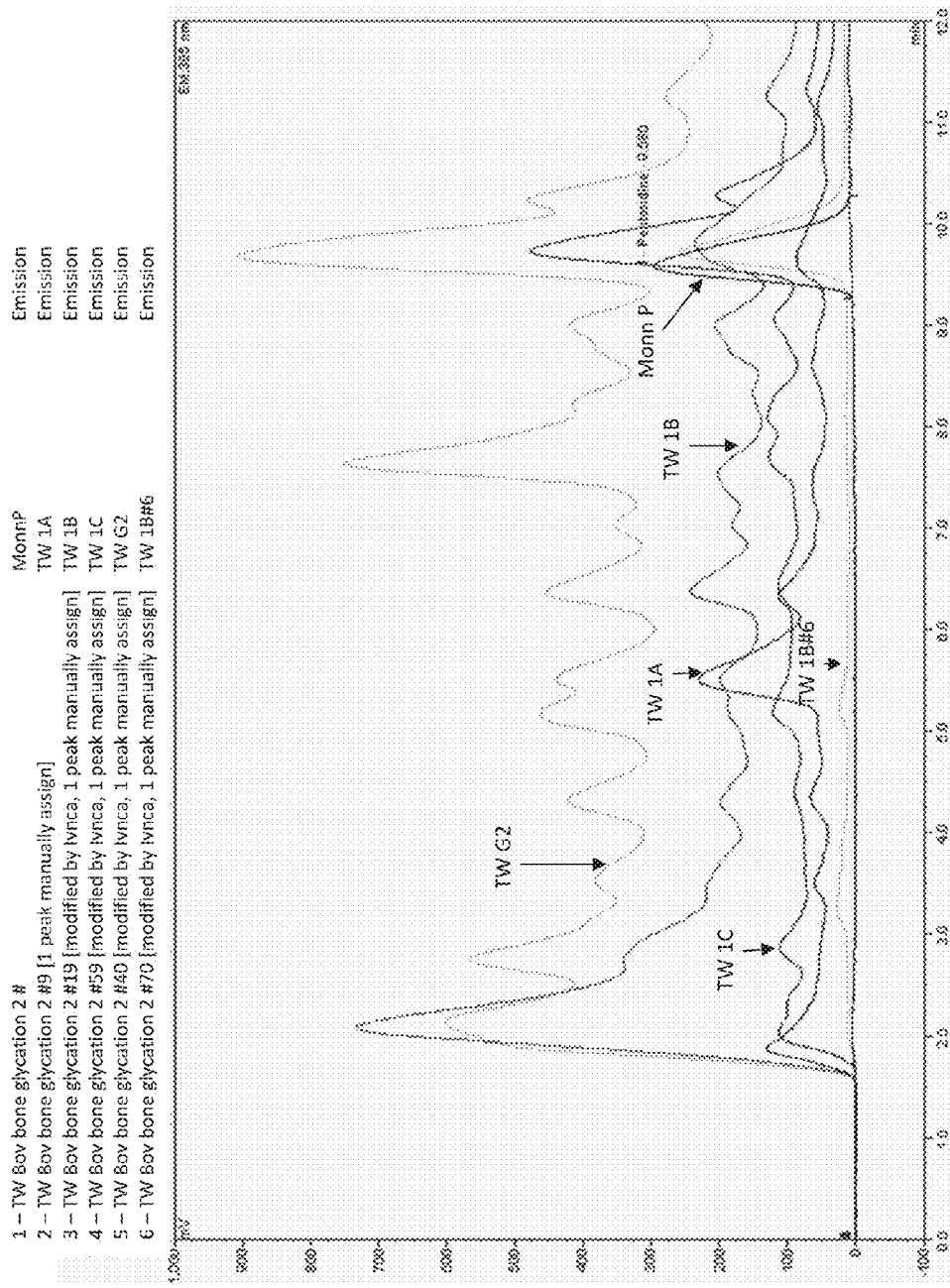
FIG. 1 shows HPLC chromatograms. MonnP—pentosidine standard; TW 1A—native bone; TW 1B—irradiated bone; TW 1C—Irradiated after 24 h 0.6M ribose pre-treatment; TW G2—Irradiated after 24 h 0.6M glucose pre-treatment; TW 1B#6—Bone incubated with 0.6M ribose for two weeks (no irradiation).

The invention provides compositions, methods, kits and systems for treating bone allografts exposed to radiation comprising an irradiation activated agent. The compositions, methods, kits and systems improve, restore, protect, increase or prevent loss of, one or more of toughness, post-yield toughness, work-to-fracture, fracture toughness and fatigue strength on exposure of the bone allografts to radiation.

Bone to be processed in accordance with the invention is generally procured under surgically sterile or aseptic conditions from donor cadavers. Once procured and preferably cleaned of soft tissues, fat and fluids, the bone is ready to be treated with the compositions and in accordance with the methods, kits and systems of the invention.

In aspects of the invention, the compositions, methods, kits and systems of the invention may be effective to improve, or prevent or minimize loss of, one or more of toughness, work-to-fracture, fracture toughness and fatigue strength on exposure to irradiation of an allograft made from bone including but not limited to a hip bone (e.g. ilium), leg bone (e.g. femur, tibiae), a bone from the spine (e.g. vertebra), or an arm bone (e.g. ulna, radius or humerus).

"Toughness" refers to the amount of work energy per unit volume needed to cause a material to fail. An increase or improvement in toughness can be found throughout the material or localized to certain portions of the material. Work-to-fracture" refers to the amount of work energy per unit of fracture surface area. "Fracture toughness" refers to the ability of a material to resist crack initiation in the presence of a defect, or of a material to resist crack propagation to the point of fracture. "Fatigue strength" refers to the range of stress needed to cause failure in a given number of cycles. "Post-yield toughness" refers to the energy (per volume) absorbed after the yield point or work done after the yield point.

Toughness, work-to-fracture, fracture toughness and fatigue strength can be measured using methods known in the art (see for example, Ritchie R O et al, Bone, 2008, 43:798-812; Koester, K J et al, Nat Mater. 2008, 7(8):672-7; Zioupos, P et al, J Biomed Mater Res A, 2008 86(3):627-36). In particular, a quasi-static three-point bend failure test (ASTM D790) may be used to measure Young's modulus, yield strength, ultimate tensile stress, failure stress/strain, toughness, resilience, post-yield toughness, work-to-fracture, and damage fraction.

In aspects of the invention the irradiation activated agent results in an about 0 to 70%, 0 to 80%, 0 to 90% or 0 to 100% restoration or protection of the toughness, post-yield toughness, work-to-fracture, fracture toughness and/or fatigue strength otherwise lost to irradiation alone. In aspects of the invention the irradiation activated agent results in a 0 to 70% restoration or protection of the toughness otherwise lost to irradiation alone. In aspects of the invention the irradiation activated agent results in a 0 to 100% restoration or protection of the toughness otherwise lost to irradiation alone. In aspects of the invention the irradiation activated agent results in a 25 to 70% restoration or protection of the toughness otherwise lost to irradiation alone. In aspects of the invention the irradiation activated agent results in a 10 to 60% restoration or protection of the toughness otherwise lost to irradiation alone. In aspects of the invention the irradiation activated agent results in a 40 to 70% restoration or protection of the toughness otherwise lost to irradiation alone. In aspects of the invention the irradiation activated agent results in a 50 to 70% restoration or protection of the toughness otherwise lost to irradiation alone. In aspects of the invention the irradiation activated agent results in a 60 to 80% restoration or protection of the toughness otherwise lost to irradiation alone.

In aspects of the invention the irradiation activated agent results in an increase in toughness, post-yield toughness, work-to-fracture, fracture toughness and/or fatigue strength of irradiated bone allografts greater than 20%, 30%, 40%, 50%, 60%, 70%, 80% or 90% compared to the toughness, post-yield toughness, work-to-fracture, fracture toughness and/or fatigue strength of the bone allografts irradiated at the same dose in the absence of the agent. In aspects of the invention the irradiation activated agent results in an increase in toughness, post-yield toughness, work-to-fracture, fracture toughness and/or fatigue strength of irradiated bone allografts greater than 20%, 30%, 40%, 50%, 60%, 70%, 80% or 90% compared to the toughness, post-yield toughness, fracture toughness and/or fatigue strength of the bone allografts irradiated at the same dose in the absence of the agent. In aspects of the invention the irradiation activated agent results in an increase in toughness, post-yield toughness, work-to-fracture, fracture toughness and/or fatigue strength of irradiated bone allografts greater than at least 30%, 40%, 50%, 60%, 70%, 80% or 90% compared to the toughness, post-yield toughness, fracture toughness and/or fatigue strength of the bone allografts irradiated at the same dose in the absence of the agent.

In aspects of the invention the irradiation activated agent results in an increase in fracture toughness of irradiated bone allografts greater than 20%, 30%, 40%, 50%, 60%, 70%, 80% or 90% compared to the fracture toughness of the bone allografts irradiated at the same dose in the absence of the agent. In aspects of the invention the irradiation activated agent results in an increase in fracture toughness of irradiated bone allografts greater than 20%, 30%, 40%, 50%, 60%, 70%, 80% or 90% compared to the fracture toughness of the bone allografts irradiated at the same dose in the absence of the agent.

In aspects of the invention the irradiation activated agent results in restored or increased connectivity of collagen matrix compared to the connectivity in the absence of the agent. In aspects of the invention the irradiation activated agent results in an increase in collagen connectivity of irradiated bone allografts greater than 20%, 30%, 40%, 50%, 60%, 70%, 80% or 90% compared to the collagen connectivity of the bone allografts irradiated at the same dose in the absence of the agent. In aspects of the invention the irradiation activated agent results in restoration of collagen connectivity of irradiated bone allografts greater than 20%, 30%, 40%, 50%, 60%, 70%, 80% or 90% compared to the collagen connectivity of the bone allografts irradiated at the same dose in the absence of the agent.

An "irradiation activated agent" refers to an agent that increases crosslinking of collagen in bone during irradiation. An agent may crosslink collagen by aldose auto-oxidation to generate ketoaldehyde compounds which react with (hydroxyl)lysine and arginine residues in a highly oxidative state, followed by oxidation and rearrangements to form adducts and crosslinks thought to be similar to Advanced Glycation Endproducts (AGEs) (13;14). An irradiation activated agent is preferably selected that is more reactive (i.e., greater crosslinking of collagen) in the presence of irradiation compared to its reactivity in the absence of radiation. An irradiation activated agent may be an organic, natural or synthetic compound. The agent can preferably be inactivated following irradiation, for example by dehydration. In aspects of the invention the agent is inactivated by lyophilization or deep-freezing.

In an aspect of the invention an irradiation activated agent is a cyclic hemiacetal or hemiketal. In an aspect of the invention an irradiation activated agent is a cyclic reducing sugar (e.g., galactose, lactose or maltose). In an aspect of the invention, an irradiation activated agent may be selected from the group consisting of lactols, aldoses and ketoses. In an embodiment, an irradiation activated agent is a pentose (e.g. ribose, arabinose, xylose and lyxose). In an embodiment of the invention, an irradiation activated agent is ribose or synthetic analogs of ribose. In an embodiment of the invention, an irradiation activated agent is selected from the group consisting of ribose and 2-hydroxytetrahydropyran. In a particular embodiment, the irradiation activated agent is 2-hydroxytetrahydropyran. In a particular embodiment of the invention, the irradiation activated agent is ribose. In a particular embodiment of the invention, the irradiation activated agent is a synthetic analog of ribose.

In an aspect of the invention an irradiation activated agent is ascorbate.

An "effective amount" of an irradiation activated agent is an amount that improves, or prevents loss of, one or more of toughness, fracture toughness, post-yield toughness, work-to-fracture and fatigue strength on exposure of a bone allograft to radiation. An effective amount may be selected that provides a selected degree of collagen crosslinking in the bone during irradiation. The degree of crosslinking may be selected based on amino acid modifications and crosslink quantification using HPLC (e.g. mols crosslink per mol collagen), or the average molecular weight between crosslinks. The extent of crosslinking may also be determined using hydrothermal isometric tension testing, gel electrophoresis and size-based column separation techniques after thermal denaturation and/or selective enzymatic digestion.

The amount of irradiation activated agent may be an amount that is sufficient to improve the toughness or work-to-fracture of an irradiated bone allograft in the range of from about 10% to about 60% using a three point bending test or tensile test. In an aspect, the amount of irradiation activated agent may be an amount that is sufficient to improve the toughness or work-to-fracture of an irradiated bone allograft in the range of from about 20% to about 50% using a three point bending test or tensile test. Three point bending tests and tensile tests are known in the art and described herein. For example, the bending test may be based on ASTM D790 [ASTM D790, "Standard Test Methods for Flexural Properties of Unreinforced and Reinforced Plastics and Electrical Insulating Materials," American Society for Testing and Materials, West Conshohocken, Pa., DOI: 10.1520/D0790-10, www.astm.org], and the tensile test may be based on ASTM D638 [ASTM D638, 2002, "Standard Test Method for Tensile Properties of Plastics," American Society for Testing and Materials, West Conshohocken, Pa., DOI: 10.1520/D0638-10, www.astm.org].

In aspects of the invention the amount of irradiation activated agent employed in a composition or method of the invention is in the range of about 0.3M to 10M, 0.5M to 10M, 0.5M to 5M, 0.5M to 2M, 0.6M to 5M, 0.6M to 2M, 0.6M to 1.8M, 1M to 1.8M, 1M to 10M, 1M to 5M, 1M to 4M, 1M to 2M, 1.5 to 1.9M, 1.6 to 1.9M, in particular 0.6M, 1.2M, 1.8M, 2.4M or 3.6M, more particularly 0.6M or 1.8M. In embodiments, the amount of irradiation activated agent employed in a composition or method of the invention is in the range of about 0.5M to 3M, 1M to 3M, 0.5M to 2M or 1M to 2M.

In a preferred embodiment, the amount of irradiation activated agent is 1.8M.

In another preferred embodiment, the amount of irradiation activated agent is 1.2M.

In another preferred embodiment, the amount of irradiation activated agent is 3M.

In aspects of the invention the amount of irradiation activated agent employed in a composition or method of the invention is less than 3M, in particular less than 2M.

The agent is added to the bone allograft for about 2 to 48 hours, 5 to 48 hours, 6 to 48 hours, 6 to 40 hours, 6 to 30 hours, 6 to 24 hours, 6 to 18 hours, 6 to 12 hours, 12 to 24 hours, 18 to 24 hours, 20 to 24 hours, 20 to 30 hours or 20 to 40 hours. In embodiment the agent is added to the bone allograft for at most 48 hours. In another embodiment, the agent is added to the bone allograft for at most 36 hours. In another embodiment, the agent is added to the bone allograft for at most 24 hours.

The agent and bone allografts are mixed at a temperature that is not deleterious to the agent or allograft, in particular about 25° C. to 80° C., 25° C. to 70° C., 25° C. to 60° C., 30° C. to 60° C., 40° C. to 60° C., 50° C. to 60° C., 50° C. to 70° C., 25° C. to 50° C., 30° C. to 50° C., 25° C. to 40° C. or 25° C. to 50° C. In an aspect, the agent and bone allografts are mixed at a temperature of about 35° C. to 40° C., in particular 37° C. In an aspect the agent and bone allografts are mixed at room temperature, optionally on dry ice. In an aspect, the agent (e.g. ribose) and bone allografts are mixed at a temperature of about 55° C. to 70° C., in particular about 60° C. to 70° C., 55 to 60° C. or 60° C. to 65° C., more particularly about 60° C.

In an embodiment, a bone allograft is pre-treated with about 1M to 2M ribose, for about 20 to 48 hours at about 55° C. to 60° C. In an embodiment, a bone allograft is pre-treated with about 1.5M to 2M ribose, for about 20 to 48 hours at about 55° C. to 60° C. In a particular embodiment, a bone allograft is pre-treated with about 1.5M to 2M ribose, for about 20 to 30 hours at about 37° C. In an embodiment, a bone allograft is pre-treated with about 1.8M ribose for about 24 hours at about 55° C. to 60° C.

An irradiation activated agent may be combined with appropriate solutes such as buffers, water, and solvents such as physiological saline, Hank's balanced salt solution and Kukobu's Simulated Body Fluid. In an embodiment, a composition is provided comprising an irradiation activated agent and a buffer, water or solvent. Other elements may be added to a composition of the invention including without limitation minerals such as calcium, phosphates, carbonates, sulfates, potassium, sodium, chloride, zinc, ascorbate, and/or magnesium. In an aspect of the invention the irradiation activated agent is combined with buffered saline, in particular phosphate buffered saline. In aspects of the invention the agent is combined with components having the composition of stimulated body fluid.

Bone allografts may undergo lipid removal prior to treatment with a composition, method, kit or system of the invention. The bone allografts may be washed with various detergents and other solvents. Lipid removal may be carried out by contacting the bone allograft with lipid solvents such as alcohols and non-ionic detergents. For example, the allografts may be washed in water and ethanol with ultrasonication and agitations (see Haimi S. et al, Biologicals 2008; 36: 99-104).

In aspects of the invention the conditions for treatment with the irradiation activated agent (i.e., amount, temperature, time etc.) are selected so that the ribose uptake is about 0.004 to 0.05 µmole/mg wet bone, preferably 0.005 to 0.02 µmole/mg wet bone, more preferably 0.005 to 0.01 µmole/mg wet bone, most preferably 0.01 µmole/mg wet bone.

The radiation employed in the methods of the invention may be any radiation effective to sterilize a tissue to be treated. Examples of radiation include, without limitation, corpuscular radiation (e.g. E-beam radiation) and electromagnetic radiation (e.g., x-rays). Typical irradiation procedures for bone allografts include gamma radiation, electron beam (E-beam) radiation, and the like. In aspects of the invention a bone allograft is subjected to gamma radiation for example, a cobalt-60 source or a cesium-137 source.

The rate of radiation may be selected based on the characteristics of the particular bone, the form of radiation involved and/or the desired amount of collagen crosslinking. Typically the rate of radiation is constant throughout the radiation procedure but in some instances it may be desirable to employ variable or discontinuous irradiation. In aspects of the invention, the rate of irradiation is at least about 3.0 kGy/hr, in particular, at least about 6 kGy/hr, at least about 15 kGy/hr, at least about 30 kGy/hr or at least about 45 kGy/hr or greater.

The bone allografts are irradiated with radiation up to a total dose effective for sterilization of the bone allograft and such total dose may vary depending on certain features such as the characteristics of the bone allograft and the form of radiation employed. Radiation dose levels are generally within the range of 25 kGy to 60 kGy, preferably 30 kGy to 50 kGy, more preferably 30 kGy, 33 kGy or 35 kGy. In aspects of the invention the radiation dose level is at least about 25 kGy, in particular 33-35 kGy. In aspects of the invention the radiation dose level is at least about 25 kGy, in particular 33-35 kGy. In other aspects of the invention, the radiation dose level is at least about 45 kGy or greater, in particular 50 kGy.

The bone allografts are irradiated with the radiation for a time effective to sterilize the allografts. A combination of radiation rate and radiation time is selected to provide the appropriate dose of irradiation to the bone allografts. Irradiation times may vary depending on the selected form and rate of radiation and the characteristics of the bone allograft. One skilled in the art can empirically determine suitable radiation times and rates to achieve the desired dose.

The invention contemplates a package for containing the bone allograft and irradiation activated agent during irradiation. The package preferably is stable under the influence of radiation, and maintains a seal against the external environment throughout the radiation procedure and post-radiation.

In an aspect, the invention provides a system for packaging a bone allograft to be exposed to radiation which comprises a container having an effective amount of an irradiation activated agent to improve, increase or prevent or minimize loss of toughness, post-yield toughness, work-to-fracture, fracture toughness and/or fatigue strength on exposure of the bone allograft to radiation. The container may comprise glass, plastic or foil, nanoporous or microporous membrane or a combination of these or other materials, and it may have a seal, in particular an airtight seal.

An irradiation activated agent in an appropriate solute can be added to the container before, after or concurrently with the placement of the bone allograft in the container. The bone allograft can be placed in the solution in the container. Alternatively, the bone allograft may be placed in the container and a solution comprising the irradiation activated agent can be added to the container via a self-sealing valve. In an embodiment, the solution is introduced in the container, preferably a sealed container, by injecting the solution through a needle inserted in a self-sealing valve in the container. The amount of solution added to the container is sufficient to provide an effective amount of the agent. In an aspect, the amount of solution is sufficient to maintain the bone allograft in a substantially submerged state. In an aspect, the amount of solution is sufficient to maintain the bone allograft in a totally submerged state. The container may be closed or sealed and exposed to radiation. Following radiation the package may be lyophilized or freeze-dried and then stored for use in a medical procedure.

Figure 3:
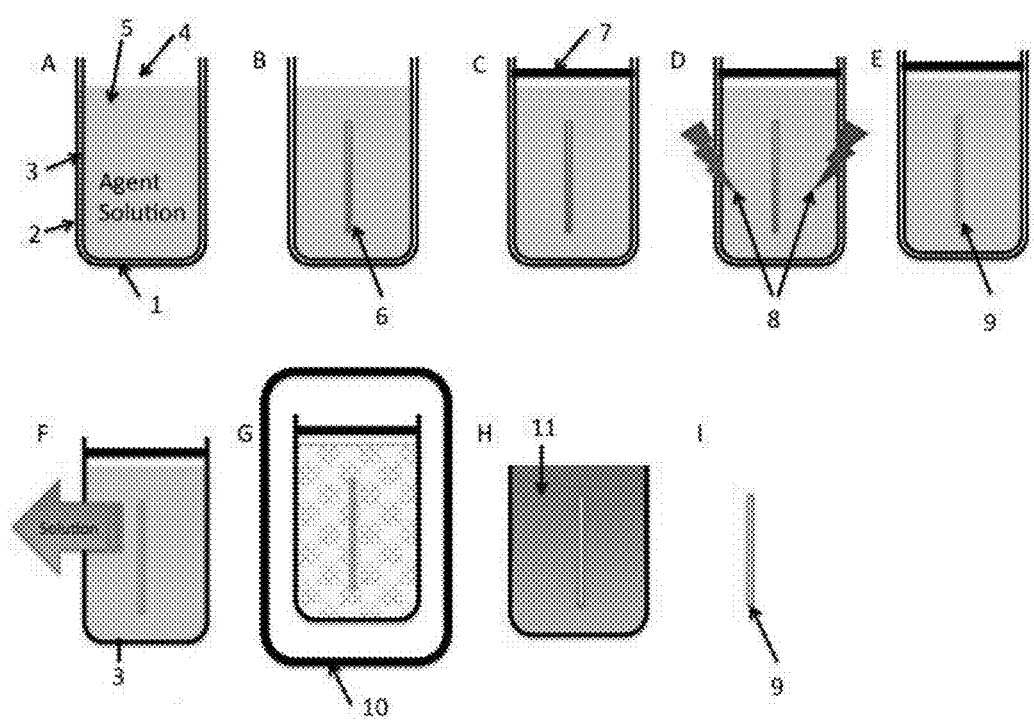
FIG. 3 is an illustration of a bone allograft processed in a double-walled container in accordance with a method of the present invention.

In an embodiment of the invention illustrated in FIG. 3, the container 1 comprises two layers or walls 2, 3 and a sealable opening 4. The outer layer 2 is impermeable, and in particular comprises an impermeable heat-sealable polymer or metal foil. The inner layer 3 is porous to the solutes used in solutions containing the irradiation activated agent and optionally porous to the agent. The inner layer 3 is also selected so that it is impermeable to contaminants and bacteria. In aspects of the invention, the inner layer 3 comprises a sub-micron porous polymer. In use the container is filled with the agent (A) in solution 5 in an amount sufficient to keep the bone allograft hydrated, and the bone allograft 6 is placed in the container (B). The sealable opening 4 is closed with an airtight seal 7 in particular it is heat-sealed (C), and the bone allograft is maintained in the container for a sufficient period of time and under suitable conditions (e.g. frozen on dry ice) prior to irradiation. The container is exposed to radiation 8 (for example, 25 or 35 kGy) (D) to produce a modified bone allograft 9 (E). Following irradiation, the outer layer 2 is separated from the inner layer 3 and the solute and optionally agent are removed (F). The solute and/or agent are preferably removed using methods that minimize activation of the agent and/or dehydration of the bone allograft. In an aspect of the invention the solute and/or agent are removed by lyophilisation/freeze-drying. In another aspect, the solute and/or agent are removed using a vacuum or suction. The bone allograft 9 within the inner layer 3 may be sealed within a sterile impermeable shell 10 for storage, typically at room temperature (G). In a medical procedure, the shell 10 and airtight seal 7 are removed under sterile/aseptic conditions, and the bone allograft 9 is rinsed with a sterile solution 11 to remove any residual agent (H) and rehydrated ready for use (I). The packaging scheme and design illustrated in FIG. 3 can be incorporated into the American Association of Tissue Banks (AATB) approved practices.

Bone allografts treated according to a method of the invention may be introduced into a subject, in particular a mammal, more particularly a human, in need thereof for prophylaxis or treatment of a condition or disease or a malfunction. Methods of introducing bone allografts into a mammal are known to those skilled in the art. Thus, the invention also contemplates use of the bone allografts treated according to a method of the invention in the prophylaxis or treatment of a condition or disease or a malfunction in a subject. In embodiments, the compositions, methods, kits and systems of the invention are used to produce allografts for use in orthopedic reconstructive surgery. In embodiments, the compositions, methods, kits and systems of the invention are used to treat large structural cortical bone allografts. Prior to introducing into a subject, a bone allograft treated according to a method of the invention may be masked at either end to maximize the contact between the host and allograft bone, preserve the host bone, and/or delay allograft rejection. In particular an artificial interface (e.g., bioengineered interface) may be incorporated at one or both ends of the treated allograft bone.

The following non-limiting examples are illustrative of the present invention:

Example 1

Triplicate bone beams from nine bovine metatarsi were tested in quasi-static three-point bending failure tests (ASTM D790). One beam from each metatarsus acted as a non-irradiated control, one as an irradiated control, and one as a pre-treated and irradiated specimen. Pre-treatment was with 0.6M ribose in phosphate buffered solution (PBS) for 24 hours at 37° C. The irradiation dose was 33 kGy on dry ice which typically causes significant deterioration of toughness. Ribose pre-treatment produced greater toughness (63% vs. 44%) and post-yield toughness (45% vs. 27%) versus irradiated controls (% of non-irradiated controls). See Table 1 below for the results of the study.

TABLE 1

| Group | Toughness (MPa) | Post Yield Toughness MPa |
|---|---|---|
| Non-Irradiated | 3.67 ± 0.84 | 2.64 ± 0.91 |
| Irradiated | 1.63 ± 0.43 | 0.72 ± 0.41 |
| Irradiated + Ribose | 2.3 ± 1.1** | 1.2 ± 1.0* |
| RM*-ANOVA p = | <0.001 | <0.001 |
| Effect of Ribose p = | 0.044** | 0.082* |

*RM = Repeated measures

Figure 2:
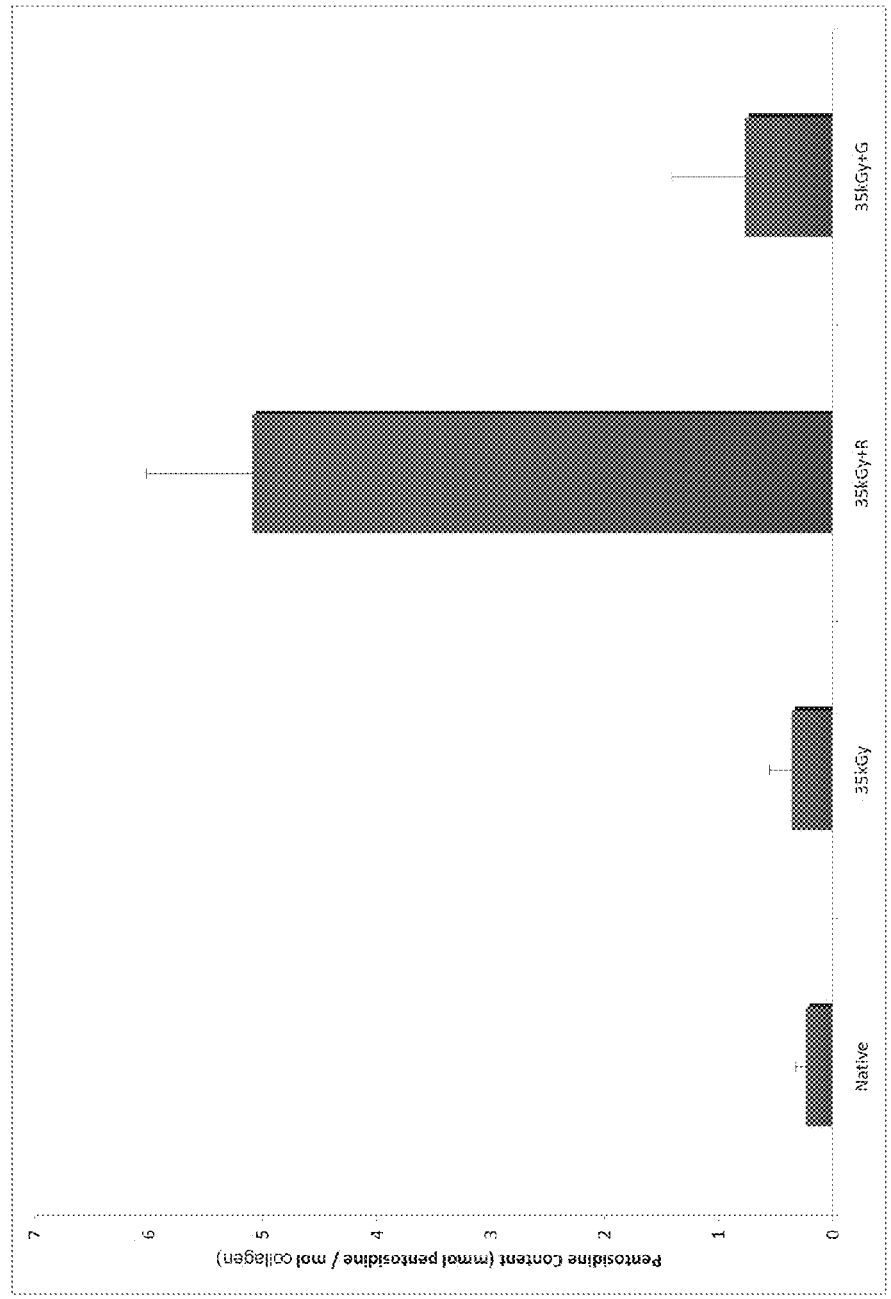
FIG. 2 is a graph showing pentosidine concentrations. Irradiation after ribose pre-treatment produces significantly greater pentosidine crosslink.

Acid hydrolysates of bone collagen from four groups (native, irradiated 35 kGY, irradiated 35 kGy+0.6M ribose, irradiated 35 kGy+0.6M glucose) were also analyzed by high performance liquid chromatography to observe the fluorescent peak profiles of each group and to quantify the concentration of the pentosidine crosslink. FIG. 1 illustrates typical chromatograms and one can clearly see the fluorescent products differ greatly between the groups. FIG. 2 shows the pentosidine concentrations. Irradiation after pre-treatment with ribose produces a different and more homogeneous set of products than glucose and avoids some of the products formed by irradiation alone. It also forms a significantly higher amount of the pentosidine crosslink than glucose.

Example 2

Human bone (male femora or tibiae; narrow age range below 55 years of age) will be used in the additional studies outlined below. The bone will be cut into beams using a band-saw and diamond wafer saw (Buehler Isomet 5000, Musculoskeletal Research Laboratory, Mount Sinai Hospital). Static three-point bend failure testing (ASTM D790) will measure Young's modulus, yield strength, ultimate tensile stress, failure stress/strain, toughness, work-to-fracture, resilience, post-yield toughness and damage fraction. Testing will be conducted using an Instron ElectroPulse E1000 universal mechanical testing machine at room temperature while hydrated using a saline drip/bath. Irradiation will be performed at Isomedix Steris (Whitby).

The experiments described in Example 1 will be repeated with three additional groups (Non-Irradiated-Lipids, Irradiated-Lipids, Irradiated-Lipids+Ribose). These new groups will first undergo lipid removal prior to pre-treatment with 0.6M ribose in PBS and then irradiation. Lipids will be removed using a known protocol involving washes in distilled water and 70% ethanol with ultrasonication and agitation (12). Extent of lipid removal will be measured biochemically after cryo-grinding using hexane extraction (12). Following irradiation, beam dimensions will be measured and the beams will be tested in three-point bending.

Experiments similar to the experiments in Example 1 will be performed with glucose and fructose to test their ability to provide increased allograft toughness. Three higher concentrations of ribose (1M, 1.8M, 2.4M, and 3.6M) will be tested to determine a dose response and approximate a preferred concentration.

The ability to irradiate at 50 kGy will also be tested with a selected agent and concentration to determine if there is a beneficial change in mechanical properties at this higher dose.

Example 3

Figure 4:
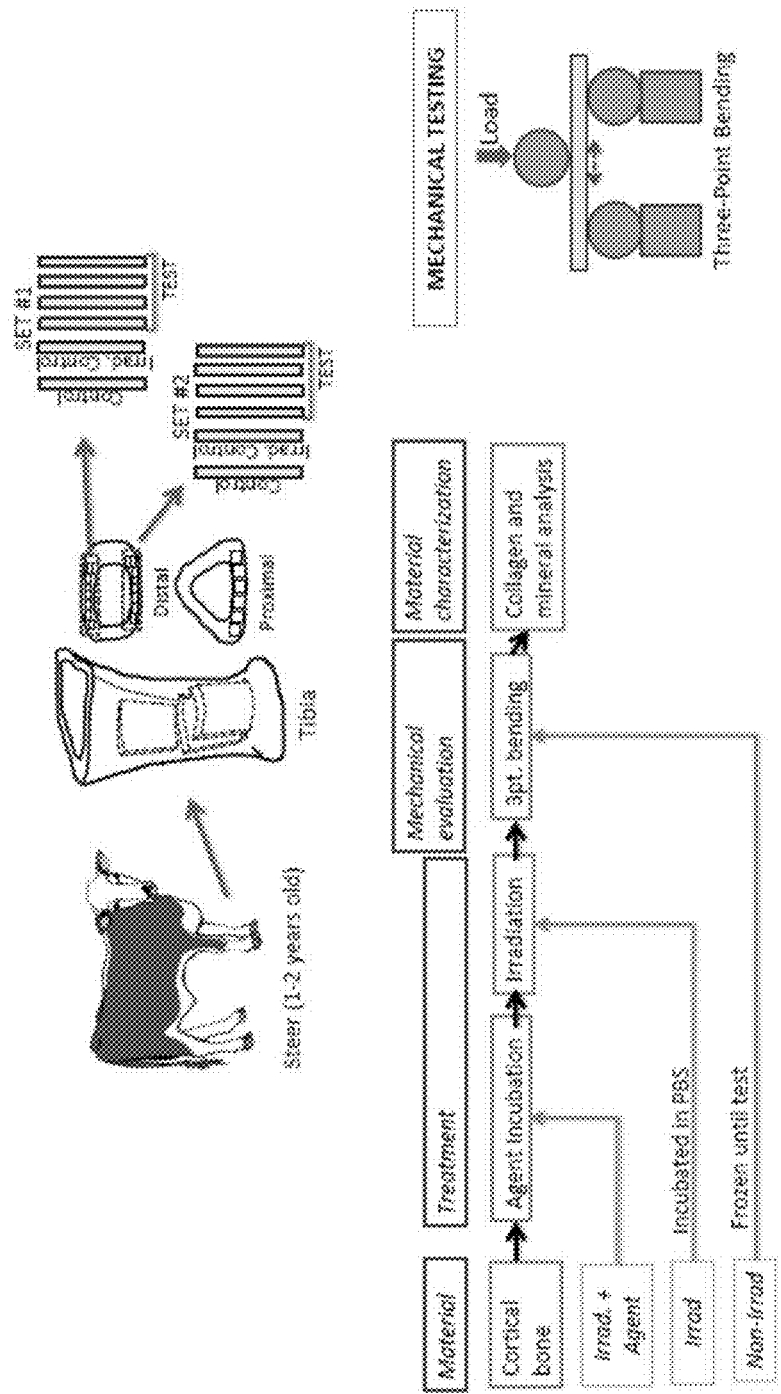
FIG. 4 is a schematic diagram illustrating methods used in the present invention.

Methods (See Schematic of a Method of the Invention in FIG. 4)

Cortical bone blocks were cut from the mid-diaphysis of bovine tibia. Three beams were cut from each block and designated to non-irradiated control (N), irradiated (I), and irradiated+agent groups (A). The agent utilized in the study described in this example was ribose, in particular 0.6M ribose. The beams were pre-treated with the agent at 60° C. for 24 hours. Each set was matched to account for biological variance (inter-animal variation). Beams were loaded until failure in 3-point bending. Strength, work-to-fracture, and elastic modulus were measured.

High Performance Liquid Chromatography (HPLC): Bone samples were decalcified and hydrolyzed, then run through a column where high pressure and harsh solvents separate and quantify collagen content and one of the many crosslinks associated with agent crosslinking.

Differential Scanning Calorimetry (DSC): Demineralized collagen is slowly heated (25° C.-85° C., ramp=5° per minute). The heat flow is measured as a function of temperature. The amount of heat needed to increase the temperature of the test sample is compared to an empty reference pan. During a phase transition (collagen denaturation), more heat is needed by the sample than the reference. The temperature at the start of the denaturation peak is $T_{onset}$. The area under the curve tells us the amount of heat absorbed during denaturation, $\Delta H$. $T_{onset}$ and $\Delta H$ are a function of the molecular structure of the collagen [13].

SDS-PAGE gel electrophoresis: Demineralized bone collagen was digested with pepsin in 0.5M acetic acid for 48 hrs at room temperature to liberate the alpha chains. Collagen was run on a 4-20% gradient gel against a reference to compare alpha and beta chain content (band intensity) and extent of fragmentation (smearing).

Hydrothermal Isometric Tension (HIT): A strip of demineralized collagen is held at both ends (in isometric constraint) while temperature is slowly increased. At a certain temperature the collagen starts to denature ($T_d$), followed by a period of increasing tension due to the driving force favoring amorphous structure of denatured collagen. Maximum Isometric force (MIF) and temperature at MIF ($T_{MIF}$) reflect the force and thermal energy required to break linkages between molecules (highest load before loss of tension) and is a function of crosslinking. MIF and $T_{MIF}$ reflect the connectivity of the collagen network [14]. (See FIGS. 5A and B)

Mechanical Testing Results

Figure 6:
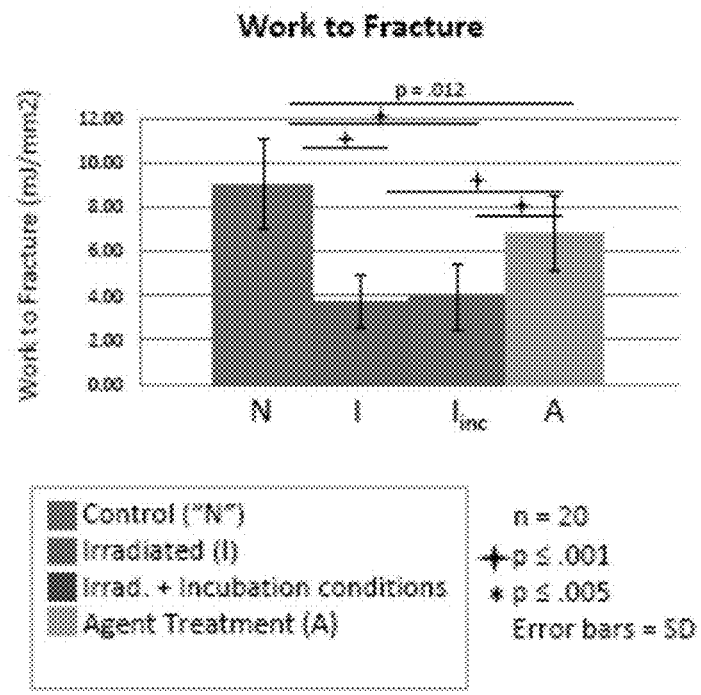
FIG. 6 is a graph illustrating work to fracture testing results. Control (N), Irradiated (I), Irradiated+incubation conditions ($I_{inc}$), and agent treatment (ribose) (A). n=20, +p≤0.001, * p≤0.005, Errors bars+SD.
Figure 7:
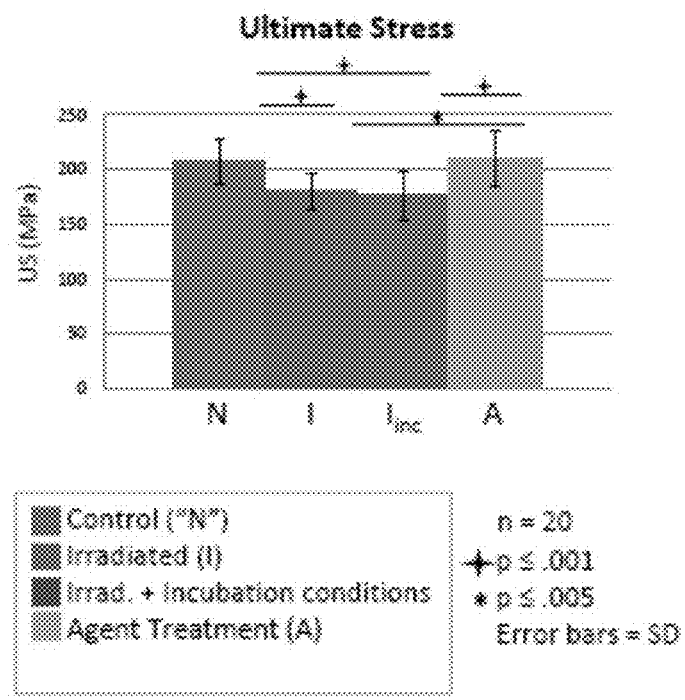
FIG. 7 is a graph illustrating ultimate stress mechanical testing results. Control (N), Irradiated (I), Irradiated+incubation conditions ($I_{inc}$), and agent treatment (ribose) (A). n=20, +p≤0.001, * p≤0.005, Errors bars+SD.

Three-Point Bending: The agent treated samples had 58% recovery of Work to Fracture and 100% recovery of Ultimate Stress. There was no significant difference in modulus for any conditions (see FIGS. 6 and 7).

Collagen Characterization Data

In DSC, a decrease in $T_{onset}$ indicates collagen degradation. An unexpected increase in ΔH indicates modification of the collagen molecules. In HIT testing, $T_d$ and MIF are significantly lowered by irradiation due to loss of connectivity. Irradiation+Agent samples recovered 48% of MIF.

Table 2 shows the results of collagen analysis and in particular the recovery of MIF in irradiation plus irradiation activated agent samples. The hydrothermal isometric tension data demonstrated a 48% recovery of maximum isometric force, and indicator of the connectivity of the bone collagen.

TABLE 2

DSC and HIT

| | | HIT | | DSC | |
|---|---|---|---|---|---|
| | | $T_d$ °C. | MIF grams force | $T_{peak}$ °C. | ΔH J/g |
| N | Mean | 57.8 | 685.6 | 62.3 | 21.3 |
|   | SD | ±1.3 | ±84.5 | ±0.9 | ±6.4 |
| I | Mean | 46.4 | 381.5 | 50.3 | 69.6 |
|   | SD | ±1.0 | ±89.7 | ±5.0 | ±7.8 |
| R | Mean | 48.2 | 528.9 | 54.6 | 49.8 |
|   | SD | ±1.1 | ±44.0 | ±5.9 | ±14.5 |
| Repeated Measures ANOVA p = | | <0.001* | 0.011* | <0.001* | 0.001* |
| N vs. I | | <0.001* | 0.004* | <0.001* | <0.001* |
| N vs. R | | <0.001* | 0.022* | 0.184 | 0.013* |
| I vs. R | | 0.313 | 0.027* | 0.135 | 0.031* |

N = non-irradiated;
I = irradiated;
R = treatment with 0.6M ribose at 37° C. for 24 hours Pentosidine is a product of the ribose reagent reacting with the collagen in the presence of the irradiation (free radicals and highly oxidative environment). This data indicates increased crosslinking due to the inclusion of an agent of the invention (i.e., ribose).

Figure 8:
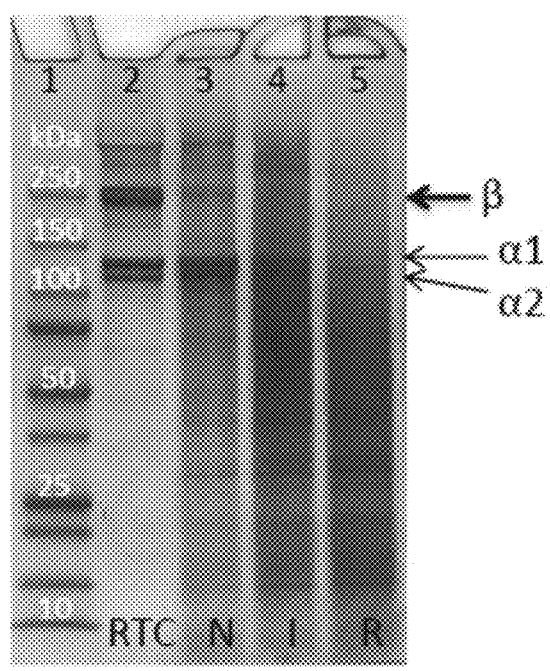
FIG. 8 shows the results of SDS gel electrophoresis in irradiated and irradiated+irradiation activated agent samples. The gel is an example from one set of samples. 4-20% gradient gel stained with Coomassie Blue. 1—Protein Ladder, 2—Rat Tail Collagen, 3—Control, 4—Irradiated, 5—Ribose treated.

Results from SDS-PAGE gel electrophoresis: In irradiated and irradiated+agent (i.e., ribose) (FIG. 8, lanes 4 & 5) there is more "smearing" and less defined alpha-chain banding. Most notably: the beta bands are missing which indicates loss of native crosslinking. Loss of alpha bands indicate alpha-chain fragmentation and smearing indicates heterogeneous fragments.

Discussion

Irradiation has deleterious effects on cortical bone mechanical properties.

Thermal analysis of demineralized collagen shows irradiation degrades collagen.

DSC and HIT data indicate modifications of collagen, particularly fragmentation of collagen molecules and overall loss of connectivity.

Mechanical tests show a significant loss in toughness after irradiation.

Recovery of both mechanical and thermomechanical properties with a treatment of the invention demonstrates an approach to improving the toughness of irradiation-sterilized bone allografts.

Figure 9:
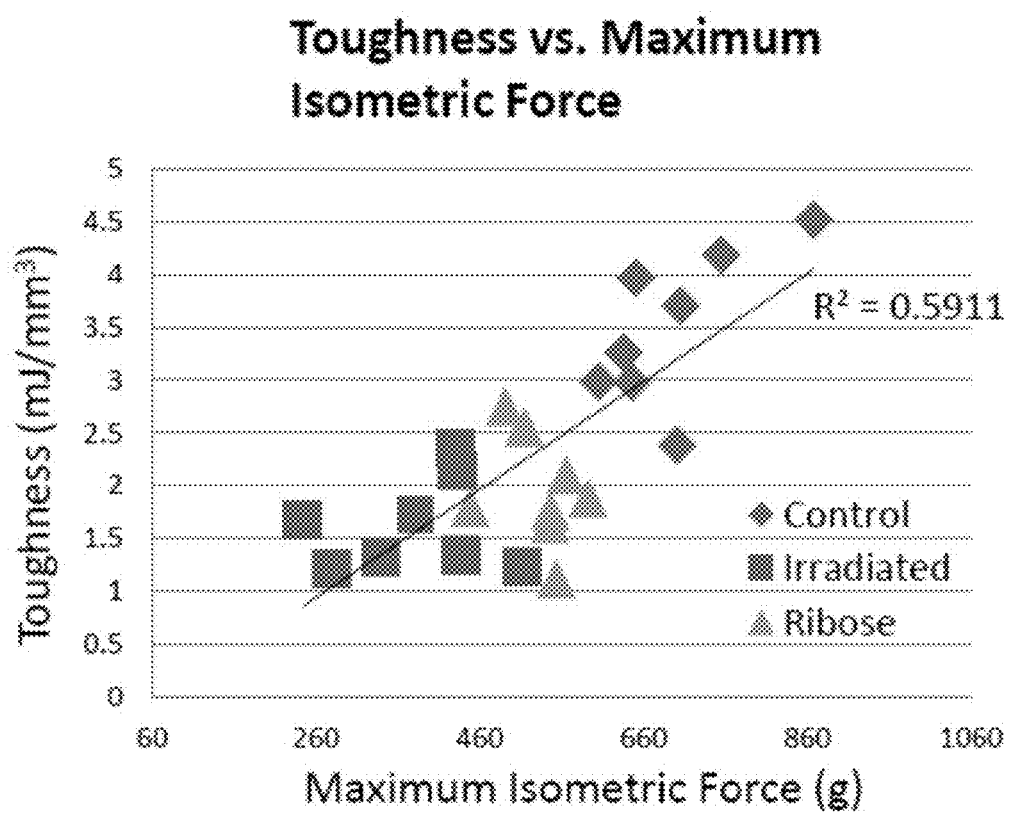
FIG. 9 is a toughness vs MIF plot showing that toughness and collagen connectivity show a positive correlation.

There is a positive correlation between toughness and collagen integrity; ribose acts on collagen via glycation and free radical polymerization; restoring the connectivity of the organic phase recovers toughness. (See FIG. 9).

Example 4

Figure 10:
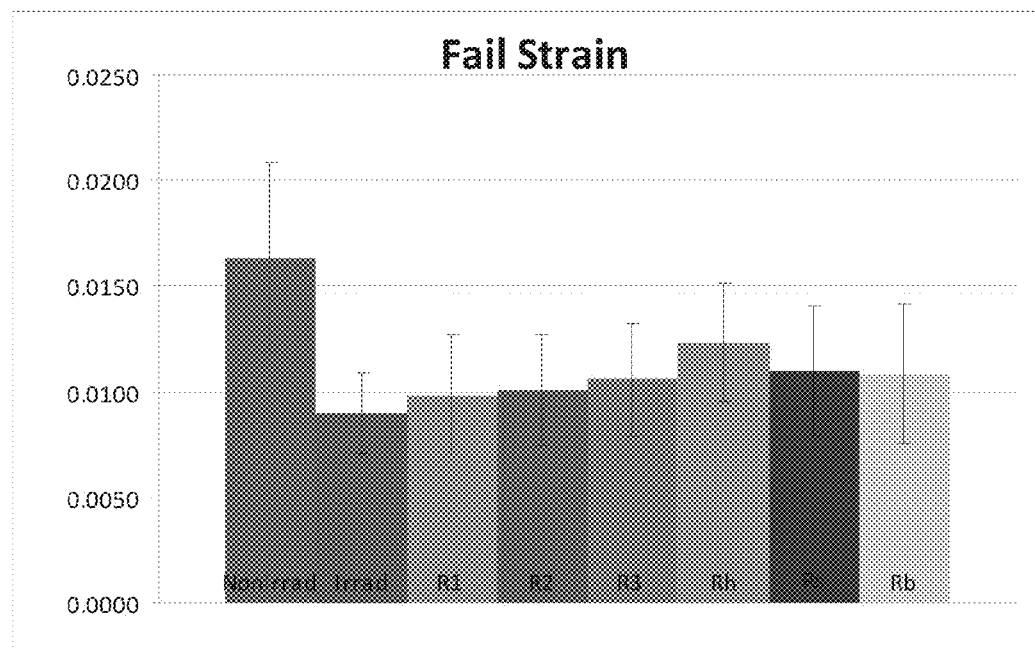
FIG. 10 shows (A) work to fracture, (B) ultimate stress, and (C) fail strain results for irradiated bovine cortical bone from the tibial diaphysis pre-treated with ribose at various concentrations and temperatures. Non-Irrad=non-irradiated control; Irrad=Irradiated; R1=0.6M @ 37° C. for 24 hours; R2=1.8M @ 37° C. for 24 hours; R3=2.4M @ 37° C. for 24 hours; Rh=1.8M @ 55° C. for 24 hours; Rs=1.8M @ 37° C. for 24 hours with sonification; Rb=1.8M @ 37° C. for 24 hours and left in solution during irradiation.

Effect of temperature and concentration. Beams from the cortical cone from the tibial diaphysis were treated with 0.6M, 1.8M, and 2.4M ribose at 37° C. and 55° C. for twenty four hours. The beams were left in solution and irradiated with a dose of 33 kGy. As shown in FIGS. 10A, B and C, the higher temperature improved toughness and strength. An increase in mean work-to-fracture or toughness (FIG. 10A), ultimate stress (FIG. 10B) and fail strain (FIG. 10C) was observed with increasing ribose concentration. A step increase in these properties was observed when pre-treatment was conducted at 55° C. rather than 37° C.

Figure 11:
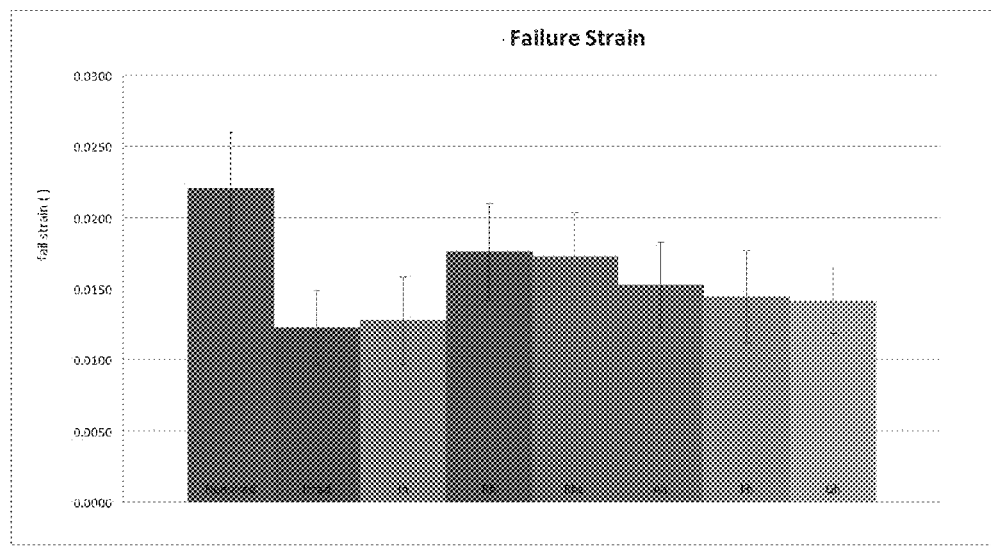
FIG. 11 shows (A) work to fracture, (B) ultimate stress, and (C) fail strain of irradiated bovine cortical bone from the tibial diaphysis pre-treated with various agents (glucose, fructose and ascorbate) and at different temperatures. Non-Irrad=non-irradiated control; Irrad=Irradiated; Ih=Irradiated control soaked at 60° C.; Rh=1.8M @ 60° C. for 24 hours; Rhs=1.8M @ 60° C. for 24 hours with sonification; Ah=ascorbate 1.8M @ 60° C. for 24 hours; Fh=fructose 1.8M @ 60° C. for 24 hours; Gh=glucose 1.8M @ 60° C. for 24 hours.

Comparison of Ribose and other Agents. Beams from the cortical cone from the tibial diaphysis were pre-treated with 1.8M solutions containing ribose, fructose, glucose or ascorbate at 60° C. for 24 hours. As shown in FIGS. 11A, B and C, ribose, followed by ascorbate, produced the greatest amount of strengthening and toughening. Ribose was superior in both restoring ultimate strength to non-irradiated control levels and in regaining 57% of the work-to-fracture (toughness) lost in the irradiated controls (FIGS. 12 A and B).

Effect of Ribose on Fracture Toughness (Resistance to Cracking) Using Single Edge Notch Bending (SENB) Fracture Toughness Testing. SENB was used to determine the elasto-plastic fracture toughness (i.e. J-integral) of treated bovine cortical bone. High temperature (60° C.) ribose pre-treatment (1.8M for 24 hours) has positive effects on the fracture toughness of irradiated bone. Pre-treatment increased the fracture toughness of the irradiated bone, demonstrating a 47% recovery (p=0.043) in J (FIG. 12A) and a 42% recovery in fracture work-to-fracture (p=0.044) (FIG. 12B).

Example 5

Ten pairs of human femurs per year from a range of donors without musculoskeletal disease will be obtained from Mount Sinai Allograft Technologies (MSAT). Optimization experiments will be conducted to confirm the optimal ribose content in human cortical bone. The bone will be cut into sets of matched beams (each pre-treated specimen will be matched to a non-irradiated control and a conventionally irradiated control), pre-treated over a range of ribose concentrations, times, and temperatures, the ribose contents of the pre-treated bone measured, and then they will be irradiated by the standard method. The beams will then undergo mechanical testing using quasi-static three-point bending and tensile testing using established methods. Specimens produced using the optimal conditions will undergo extensive mechanical testing, including fracture toughness testing and fatigue testing, matrix characterization and strengthening and toughening mechanism studies using established methods in order to further verify the results and to confirm the nature of the modified bone and the source of strengthening and toughening. The optimal conditions will be further tested after irradiation at 50 kGy using the same set of tests previously described.

Beam Cutting: Test specimens will be cut from the diaphysial cortical bone with their lengths aligned with the longitudinal direction of the cortex. The rectangular beams will be cut using a Buehler Isomet 1000 metallurgical saw (Musculoskeletal Research Laboratory, SLRI, MSH) with diamond wafer blade and then wet ground and polished by hand to the required dimensions and finish. For the single edge notch bend fracture specimens, the notch and side grooves will be cut to ASTM E1820 specifications [15]. The notch will be sharpened to a <10 µm radius "micro-notch" using a razor blade lubricated with 1 µm diamond paste.

Bone Characterization (Inputs): Variability in bone mineral density, porosity and collagen crosslinking, composition and nativity will be accounted for statistically by treating them as co-variants in the statistical analyses. Following beam preparation, specimen geometry, porosity and volumetric bone mineral density (vBMD) will be measured using micro-computed tomography (SkyScan 1174, SkyScan, Belgium; Musculoskeletal Research Laboratory, SLRI, MSH). The pre-existing bone collagen crosslinking and amino acid composition will be examined using established high performance liquid chromatography methods. Mature enzymatic crosslinks (lysyl-pyridinoline (L-Pyr), hydroxylysyl-pyridinoline (H-Pyr)), pentosidine (Pent) and hydroxyproline (OH-Pro) contents will be measured [16].

Pre-Treatments: A range of ribose contents will be achieved by pre-treatment under various conditions. The range of ribose solution concentrations and temperatures is constrained by practicality. Ribose solutions become very viscous above 3M and viscosity slows diffusion. Temperatures above 70° C. can be damaging to bone. Time can be varied within a practical range of one to 48 hours.

Measurement of Ribose Content (Inputs): After pre-treatment and prior to irradiation, a small portion of each beam will be removed from one end using the metallurgical saw. The portion will be cryoground (liquid nitrogen) to a fine powder and lyophilized. The dry mass will be measured using an analytical balance and then the powder will be simultaneously decalcified and washed with dilute acetic acid for 24 hours to release the ribose from the matrix into solution. The ribose content of the wash solution will then be measured using spectrophotometry by derivatization of the carbonyls with 2,4-dinitrophenyldydrazine in SDS-containing buffer and measuring absorption at 360 nm [17]. Ribose contents will be determined using a ribose concentration versus absorption standard curve.

Irradiation: Specimens designated for irradiation will be packaged on dry ice using established tissue banking protocols and techniques and sent to Isomedix Steris in Whitby, Ontario, Canada. The specimens will then be irradiated with a dose of 30 kGy±3 kGy while on dry ice.

Mechanical Testing (Outputs): Mechanical tests to failure will be conducted using standard point bending and tensile tests. Mechanical testing will be conducted using an Instron ElectroPuls E1000 mechanical testing machine (Musculoskeletal Research Laboratory, SLRI, MSH). The bend testing will based on ASTM D790. Tensile testing will be based on ASTM D638. From the test data, the elastic modulus, yield strength, ultimate stress, yield strain, strain to failure, toughness and work-to-fracture will be calculated.

Fracture Toughness Testing: Fracture toughness testing provides the means for measuring bone's resistance to crack propagation and its defect tolerance. Single edge notch bend (SENB) specimens will be rehydrated in PBS for at least two hours and then tested in three-point bending using the same apparatus for the 3ptB testing described herein. All SENB specimen preparation and testing will be conducted by closely following specifications given in ASTM E1820 [ASTM E1820, "Standard Test Method for Measurement of Fracture Toughness," American Society for Testing and Materials, West Conshohocken, Pa., DOI: 10.1520/E1820-11, www.astm.org]; the established standard for fracture testing of materials exhibiting elastic-plastic behaviour. This standard has been previously applied to the testing of cortical bone [18-21]. The J-integral fracture toughness will be measured at crack propagation initiation and crack instability as well as the total work-to-fracture [18, 22]. The mechanical testing machine will be programmed to stop each test when instability is reached (zero slope). This will allow all of the necessary measurements to be made while keeping the test specimen in one piece, facilitating the next step in which the fracture specimens will be stained using the $BaSO_4$ precipitation technique [23]. In doing so, the damage volume (DV) around the crack can be quantified and normalized to the bone volume (BV). % DV/BV can be compared between matched specimens; this provides a measure of the microdamage formation capacity of the bone. Microdamage formation is an important toughening mechanism because it supplies pseudo-plasticity. A reduced capacity may explain reduced fracture toughness in the irradiated specimens and a restored capacity may explain improved toughness in the treated specimens. Additionally, the models generated with microCT after $BaSO_4$ precipitation allow three-dimensional measurement of the stable crack propagation, providing further information regarding the toughening mechanisms at play. Subsequently, following the methods of Yan et al [18, 22], micro-notch, side groove dimensions and the crack propagation lengths at instability are easily measured based on distinct fracture surface morphologies observed using scanning electron microscopy.

Tensile Fatigue Testing: Each fatigue designated specimen and its matched controls will be fatigue tested under tension-tension conditions. Whole-life fatigue data (S-N curves) will be generated for the non-irradiated, irradiated and ribose pre-treated groups. Fatigue testing will be conducted using an Instron ElectroPuls E10000 mechanical testing machine (Musculoskeletal Research Laboratory, Mount Sinai Hospital). Following fatigue testing, the specimens will be stained using the $BaSO_4$ precipitation method and scanned using microCT as described above [24]. % DV/BV will be compared between the controls and ribose pre-treated specimens.

Matrix Characterization (Outputs): Collagen Fibril Ultrastructure: Irradiation is known to fracture the collagen alpha chains [11] and to break collagen crosslinks. It will be determined if the collagen ultrastructure is better maintained in the pre-treated specimens versus conventionally irradiated bone. The collagen ultrastructure will be examined by transmission electron microscopy using established protocols.

Collagen Network Connectivity and Crosslinking: This will be quantified using both hydrothermal isometric tension (HIT) testing and the HPLC methods discussed herein. HPLC enables the accurate and precise quantification of known crosslinks such as the enzymatically-derived collagen crosslinks and the glyco-oxidation crosslink, pentosidine [16]. HIT testing is a thermomechanical test that allows the quantitative examination of the collagen network connectivity [25].

Collagen Nativity and Degradation: SDS-PAGE: Collagen degradation due to irradiation will be measured by isolating the bone collagen from a portion of each bone beam using decalcification and pepsin digestion and then measuring the amounts of intact alpha and beta bands by gel electrophoresis (SDS-PAGE). The collagen from the irradiated beams will be directly compared with collagen from non-irradiated controls. Extensive fragmentation of the collagen due to irradiation will result in weak or lost α and β bands and channel smearing [11]. In specimens with extensive glycol-oxidation crosslinking, alterations in band location (peptide size) and band intensities are expected. SDS-PAGE will confirm the nature of the glycol-oxidation crosslinking modified bone collagen.

Selective Digestion: SDS-PAGE only allows investigation of collagen fragmentation and crosslinking (to a limited degree). Therefore, an additional portion of each beam will be demineralised and used to measure the collagen's resistance to specific proteolysis by a gelatinase to further assess damage/denaturation. The amount of degraded collagen molecules, expressed as the percentage of the total amount of collagen, will be determined using a selective digestion technique where the collagen is digested at 37° C. for 24 h in α-chymotrypsin solution [26, 27]. Selective digestion with α-chymotrypsin-TLCK (CDTLCK, Worthington Biochemical Corp., NJ, USA) digests only damaged/denatured collagen, whereas the intact collagen molecules remain insoluble [26, 27]. α-Chymotrypsin-TLCK cuts proteins specifically at phenylalanine, tyrosine and tryptophan and therefore the crosslinking at arginine and lysine should not mask the ability of this assay to measure collagen damage [27, 28].

Differential Scanning Calorimetry (DSC): DSC is a thermal analysis technique which can provide valuable information about the molecular and intermolecular state of the collagenous network. Thermal characteristics and behavior can be correlated to characteristics of collagen structure, most importantly crosslinking [29], intermolecular lattice structure [30] and degradation [31, 32]. Changes in the thermal properties of collagen due to damage in vitro and in vivo are well documented [13, 14, 28, 31, 32]. A portion of each beam will be decalcified prior to DSC on a TA Instruments DSC Q2000 calorimeter (Dr. Ning Yan, Department of Forestry, University of Toronto) and scanned from 25 to 100° C. at 5° C. per min [13]. Afterwards, the amount of collagen in the pans will be verified using a hydroxyproline assay in order to normalize heat absorbed to collagen content. Nativity of the collagen structure will be compared between groups by their ΔH values. ΔH is the amount of heat required to melt the collagen normalized to the amount of collagen present and is effectively reduced to zero by complete denaturation of collagen. ΔH values are expected to fall close to those of native bone collagen with ribose pre-treatment [13, 14, 28].

Example 6

Sterilization Effectiveness

An experiment will be conducted to test whether the methods described herein have an effect on bacterial burden and sterilization effectiveness. The study will be based on a study by Kattaya et al. in which they tested the effect of novel radioprotectant and radiosensitizer solutions on sterilization effectiveness [33]. The effect of the optimal ribose pre-treatment conditions will be tested on bacterial spores (*Bacillus pumilus*, $10^6$ spores per strip, NAMSA, Northwood, Ohio, USA). Four experimental groups will be used: 1) a non-pre-treated, non-irradiated control group, 2) a non-pre-treated, irradiated control group, 3) a pre-treated, non-irradiated group and 4) a pre-treated, irradiated group. The spore strips will be handled under laminar flow hood conditions and placed in sterile 50 ml falcon tubes. For groups 3 and 4, the spore strips will be placed in 40 ml of 0.2 µm sterile filtered pre-treatment solution and incubated under the optimal conditions. Subsequently, groups 2 and 4 will be sent for irradiation (30 kGy on dry ice; Isomedix Steris). The irradiation dose will be confirmed using Perspex gamma-ray dosimeters (Harwell Ltd., Oxford, UK). Upon return from irradiation, the spore strips in their sterile falcon tubes will be delivered to the Department of Microbiology at Mount Sinai Hospital. The spore strips will be incubated in rotating incubators in tryptic soy broth media for two weeks at 35° C. and then serially diluted and plated on Petri dishes with tryptic soybean-casein digest agar and incubated for 24 h at 37° C. Colony counting will be performed to determine if a) bacterial growth occurs during the pre-treatment phase (difference between groups 3 and 1) and b) if the pre-treatment solution provides the bacteria protection from the irradiation (difference between groups 4 and 2). One expects that 30 kGy of irradiation should provide a $10^{-6}$ reduction in spore count and therefore group 2 should not grow. The same is expected of group 4 if the pre-treatment solution is not protective.

Example 7

The bone graft material produced by the methods described herein will be tested for their potential for osteo-compatibility, osteo-conduction and graft-host union rate and strength compared to conventionally irradiated bone allograft. The accepted and widely used critical size segmental defect of the mature rabbit radius model [34] will be used. New Zealand White rabbits are an established model for studying skeletal graft materials, partly because they have human-like osteonal remodeling and microstructure. Using only one breed of rabbit the effect of the treatment will be tested without complications due to host response to allograft bone. Thirty female retired breeder New Zealand White rabbits (greater than 28 weeks old) will be sourced from Charles River Laboratories, kept at the Division of Comparative Medicine at the University of Toronto. They will be randomly divided into two recipient groups of fifteen. One group will be designated to receive a conventionally irradiated allograft (30 kGy on dry ice). The second group will receive an allograft produced with the optimized pre-treatment method (Example 5). The allografts will be produced using the right radii from thirty additional weight-matched donor female retired breeder New Zealand White rabbits. The diaphysis of each radii will be separated from the rest of the bone and all soft tissues and marrow will be removed mechanically by manual scraping and high pressure water sprayer. Each oversized radii shaft will then be matched to a recipient rabbit based on weight and radiographic matching. Once matched, the allografts will proceed through one of the two irradiation sterilization methods. The surgical model and protocol will be based on the established model and protocol published in An and Friedman's Animal Models in Orthopaedic Research [34] Under appropriate sedation and anesthesia, a longitudinal skin incision is made over the radial bone at the middle one third of the front right leg. The periosteum is carefully separated from the surrounding muscles and a critically sized 20-mm defect (>2× bone major diameter) located approximately 2 to 2.5 cm proximal to the radiocarpal joint is created in the right radius of each of the recipient rabbits using a circular saw. The defect site will be cleaned and the previously matched allograft will be cut to establish a tight press fit between the graft and the host bone. The graft will be held in place by circlage wires and the surgical site closed. Appropriate analgesia will be administered post-op and the reconstruction and healing will be followed with weekly x-rays. Fluorescent bone formation markers (calcein green, xylenol orange and alizarin red), which enable later dynamic histomorphometry, will be administered nine weeks, five weeks and one week prior to sacrifice at 16 weeks post-op. After sacrifice, the reconstructed radii will be dissected, cleaned of surrounding soft tissues and halved transversely at mid graft. One half of the specimen will be fixed in formalin, scanned with microCT to examine the host-graft union and then embedded in Spurr resin in preparation for histological examination and static and dynamic histomorphometry. Using static and dynamic histomorphometry, the host-graft junction will be examined and the amount of osteo-conduction and revitalization of the graft material will be measured. The other half will be immediately scanned using microCT to again examine the host-graft union and then mechanically tested in torsion to measure the strength of the union using an Instron E 10000 mechanical testing machine.

Example 8

A series of experiments will be conducted to measure the diffusivity of ribose in human cortical bone and to understand the variables that can affect this diffusivity (such as porosity and bone mineral density). The diffusion coefficient (D) of ribose through cortical bone will be determined by using a one-dimensional steady state diffusion cell setup custom built using the cylindrical portion of a human femur and using the steady-state ribose flux and concentration gradient data to calculate D using Fick's 1st Law [35]. How D is influenced by pre-treatment conditions such as temperature and donor bone variables such as porosity and bone mineral density (measured with microCT) will be determined. D is a function of temperature and temperature-independent constants ($D_0$, and $Q_d$) and can be determined by fitting D vs T data to the Arrhenius Equation in the form: $\ln D = D_0 - Q_d/R \times (1/T)$ [35]. Using the data and applying Fick's 2nd Law, the diffusion processes will be mathematically modeled (in MatLab) in the more complicated soaking situations that are expected in tissue banking processes. These mathematical models will allow one to estimate the pretreatment conditions required to achieve an evenly distributed optimal dose of ribose. The predictions of the mathematical models will be confirmed by using the ribose quantification method described herein, taking advantage of the reaction of 2,4-dinitrophenyldydrazine with the carbonyl group on the ribose, which produces a product measurable with spectroscopy [17]. Additionally, using 2,4-dinitrophenyldydrazine as a histological stain, the spatial distribution of the ribose will be tested. Sections will be cut using a diamond wire saw (100s of microns thick), stained, and imaged using an automated tiling light microscope running Visiopharm image acquisition and analysis software (Pathology and Lab Medicine, Mount Sinai Hospital).

Example 9

Ribose Pre-Treatment to Improve Bone Mechanical Properties

In this study, bovine bone beams were evaluated in 3-point bending for mechanical properties, radiographically for bone mineral density, and with several collagen characterization techniques. The objective of this study was to evaluate ribose treatment as a method to improve the toughness of irradiated bone. This was achieved by comparing the performance of ribose pre-treated and irradiated bone to that of non-irradiated bone and irradiated bone with no treatment.

The following methods were used in the study.

Sample Preparation. Eight tibia bones from steers (aged 2 years old) were obtained immediately after slaughter from a local abattoir and kept frozen (−20° C.) for 3-10 days until dissection. Frozen bones were thawed stripped of all soft tissue (muscle and fat). The periosteum was scraped from the bone surface using a surgical scalpel. Using a band saw, bones were cut into blocks approximately 70 mm×25 mm×6 mm with three blocks from each bone: distal anterior, distal posterior, and proximal as shown in FIG. 4. The location and animal number was noted and blocks were stored frozen until further processing. A total of 16 blocks from 8 tibias were used. Only distal anterior and distal posterior blocks were processed further because the proximal blocks had irregular shapes making it difficult to ensure the correct orientation and consistent microstructure in each of the specimens. Later, each block was cut into rectangular beams with the length along the longitudinal dimension and the thickness in the radial direction with an Isomet 1000 diamond wafer saw (Buehler Canada, Whitby, ON, Canada). Beams had the dimensions of 60 mm×4 mm×2 mm (l×w×t). The endosteal side of the beam is marked with a permanent marker to keep track of orientation. The beams from each block (10-20 per block) were kept together as a matched set. The beams were randomly assigned to be a non-irradiated control, irradiated control, or one of the ribose test groups including: low concentration ribose treatment, medium concentration ribose treatment, high concentration ribose treatment, and medium concentration+high temperature ribose treatment (see Table 3 for concentrations and conditions).

TABLE 3

Treatment Conditions Prior to Irradiation

| Sample Name | Treatment | Incubation solution | Conditions: time/temp |
|---|---|---|---|
| NonIrrad | None | None | Frozen until testing |
| Irrad | Irradiation | PBS | 24 hrs/37° |
| Ribose 1 | Ribose conc. Low | PBS + 0.6M D-Ribose | 24 hrs/37° |
| Ribose 2 | Ribose conc. Med | PBS + 1.8M D-Ribose | 24 hrs/37° |
| Ribose 3 | Ribose conc. High | PBS + 3M D-Ribose | 24 hrs/37° |
| High T Ribose | Ribose high temp | PBS + 1.8M D-Ribose | 24 hrs/55° |

Each set of beams was kept matched with controls from the same animal and block. A set includes one non-irradiated control, one irradiated control, and one of each of the test specimens. By matching controls to each test sample from the same location on the same animal, any differences resulting from comparison of one animal to another are reduced. Bone is extremely heterogeneous in microstructure, which is why the beams from each group were also matched with beams as closely together as possible in the same plane. Further analysis, however, showed no significant difference in non-irradiated beams from different locations. Matching each treatment group to a control from the same animal and location will account for a variation in statistics and provide more power to statistical comparisons between groups.

A non-destructive screening test was performed prior to further testing to screen for beams with major defects (i.e. large blood vessel) that would affect the mechanical performance. All beams from one set were soaked in PBS for 30 minutes. Beams were loaded endosteal side-up into a custom three-point bend fixture in an Instron E1000 mechanical testing machine with a 100N load cell. The beams were loaded up to 100 MPA which is known to be well below the yield point so that any deformation was elastic (non-permanent). The flexure modulus was calculated as the slope of the stress-strain curve. Beams with moduli two or more standard deviations away from the group mean were not used in an effort to start with uniform groups and eliminate any pre-treatment differences. After the test, the beam was unloaded and wrapped in saline soaked gauze. At the end of all sample preparation methods, there were 16 matched sets containing 6 beams each. All samples were wrapped in saline soaked gauze, stored individually in empty 15 mL centrifuge tubes, and frozen at −20° C.

Treatment. Sixteen matched sets of cortical bone beams were used. Each set contained one of each of the following six groups: Non-Irradiated, Irradiated, Ribose 1 (0.6M ribose solution), Ribose 2 (1.8M ribose solution), Ribose 3 (3.0M ribose solution), and High T Ribose (1.8M ribose solution at 55° C.). Control bones were untreated and left in the freezer (−20° C.) until mechanical testing. The Irradiated group was incubated in PBS for 24 hours (prior to irradiation) at 37° C. to control for the incubation conditions of the test groups. Solutions were prepared by dissolving powdered D-Ribose (Sigma Aldrich) into PBS to the appropriate concentration and adjusting the pH to 7.4 with dilute HCL or NaOH as needed. Samples (aside from the controls) were placed in tubes with 45 mL of their respective solutions and left to incubate for 24 hours. High T Ribose was the only group to be incubated in a water bath at an elevated temperature of 55° C. (all other groups were incubated in a warm room at 37° C.). See Table 3 for a list of the treatment conditions. The three different concentrations of ribose in solution were tested to measure mechanical performance depending on concentration. In addition, the high temperature (55° C.) incubation condition was tested as an attempt to increase the diffusion of ribose into the bone and possibly increase crosslinking action. Following incubation, all samples were wrapped in saline soaked gauze, stored individually in empty 15 mL centrifuge tubes, and frozen at −20° C.

Irradiation. Irradiation was performed with the help of Allograft Technologies at Mount Sinai Hospital. Briefly, all samples were packed in the center of a box surrounded with dry ice and sent to Steris Isomedix (Whitby, ON) where it was irradiated at ~30 kGy from a Cobalt-60 gamma irradiation source. The box was received within 24 hours of irradiation and samples were transferred into the freezer until testing.

Three-point Bending. Following Irradiation, bone beams were thawed at room temperature and polished by hand to a 1-um finish. Immediately after polishing, beams were placed in 15 mL PBS to soak for 4 hours (at room temperature) prior to testing in order to rehydrate the sample. Three-point bending tests to failure methods were based on the ASTM D790. Measurements of thickness and width were taken immediately before testing using a micrometer and entered into the computer test method before testing each beam. The beam was held by two circular supports (diameter 6.35 mm) separated by a span of 40 mm (span to thickness ratio>20:1). The beams were oriented so that the periosteal side of the bone beam was facing down (this face will be in tension during loading). A crosshead (diameter 6.35 mm) was lowered onto the center of the test beam at a constant loading rate of 1.04 mm/min based on the following equation from ASTM D970:

$$R = \frac{ZL^2}{6d}$$

Where R is the loading rate, Z is the strain rate (equal to 0.005), L is the span (equal to 50 mm) and d is the beam thickness.

The applied load was measured using a calibrated 100N load cell. The position of the crosshead, time, and load was recorded using Instron Bluehill data acquisition software. The three-point bending tests were conducted using an Instron E1000 mechanical testing device with custom made fixtures. From the load and displacement data, a stress-strain curve was created from which various mechanical properties are calculated. The following parameters were determined from the stress-strain curve: elastic modulus (E), yield stress ($\sigma y$), yield strain ($\epsilon y$), ultimate stress ($\sigma u$), work to fracture (WFx), and failure strain ($\epsilon f$).

Dual Energy X-Ray Absorptiometry. Dual Energy X-Ray Absorptiometry (DEXA) was performed on half of the beam from each sample after failure in three-point bending. Samples were scanned one at a time on a polymer tray with positioning markers in the same orientation to avoid variations based on placement in the machine. The bone mineral density (BMD) of each specimen was measured using a PIXImus dual energy x-ray absorptiometer. A measure of bone mineral content was divided over the projected area of the sample surface. Measurements of thickness of the samples were taken (using digital vernier calipers) at three locations and then the bone mineral content was divided by average thickness to obtain an estimate for the volumetric bone mineral density (bone mineral content/area×thickness).

Collagen Characterization. Of the groups tested in 3-point bending, four were selected for collagen characterization (Non-Irradiated control, Irradiated, 1.8M Ribose at 37° C., and 1.8M Ribose at 55° C.). These groups were of interest because the High T Ribose group had the best recovery of toughness and the 1.8M Ribose group was chosen as a comparison since it was treated with the same concentration of ribose but at a temperature of 55° C. instead of 37° C. Portions of the fractured beams located away from the fracture site were taken for collagen characterization. These portions of the bone beams were demineralized in EDTA for 3 weeks at room temperature, and then prepared for each of the collagen characterization methods. The methods summarized below were repeated with these samples. Following is a brief summary of each method.

When investigating collagen fragmentation with SDS-PAGE, samples were demineralized and ground into a fine powder, then digested with pepsin to liberate individual collagen triple helices. The digested solution was centrifuged to separate the soluble proteins in the supernatant and the insoluble fraction in the pellet. The soluble supernatant was filtered, mixed with Laemmli sample buffer containing SDS, and run on a polyacrylamide gel where proteins are separated based on molecular weight. The uniformity of the gamma, beta, and alpha chains of collagen results in distinct bands and heterogeneous fragments will appear as a smear. In this study, some of the insoluble pellets were freeze-dried and weighed. This weight was compared to the starting the weight, and the percent matrix solubilized was calculated (dividing the difference between the starting and pellet weight by the starting weight) in order to determine susceptibility to pepsin digestion.

Pentosidine crosslinks were quantified using HPLC in order to determine if ribose pre-treatment was in fact crosslinking collagen. The concentration of pentosidine in the sample was normalized to the amount of collagen in the sample using a colorimetric assay for hydroxyproline. In order to measure thermal stability, differential scanning calorimetry was used. Demineralized bone was heated slowly and the heat flow was measured, which records a peak during the denaturation that can provide information about the thermal stability of the helix. Hydrothermal isometric tension testing was used to evaluate thermomechanical properties and give a measure of collagen connectivity. Strips of demineralized collagen were slowly heated and the increase in tension created by the driving force for amorphous coils to shrink was recorded. From this curve, several parameters are calculated that reflect the connectivity of the material.

Statistical Analysis. The data are all presented as mean±standard deviation, with a p value of less than 0.05 considered statistically significant. Statistical analysis was performed using SPSS v18 (SPSS, Chicago, Ill., USA). One-way repeated measures ANOVA (RM ANOVA) was used to detect differences between the means of each group. Repeated measures ANOVA considers each sample within its matched set, which controls for inter-animal variance. A Holms-Sidak post-hoc analysis was used for multiple comparisons between groups when significance was detected using RM ANOVA. The adjusted p-values are reported when discussing a comparison between two groups.

The results of the study are described below.

Mechanical Properties. The results of three-point bending showed irradiation and ribose treatments had an effect on ultimate stress, failure strain, and work to fracture while modulus, yield stress, and bone mineral density were unaffected. See Table 4 (below) for mechanical properties and Table 5 (below) for bone mineral density data. On average, Irradiated samples had 20% lower ultimate stress (p=0.003), 62% loss of work-to-fracture (p≤0.001), and 45% loss of failure strain (p≤0.001) compared to the non-irradiated control. The 0.6M Ribose treatment was essentially ineffective, with no parameters significantly different from the Irradiated group. It was also the only group with significantly lower yield strain (p=0.019, compared to Non-Irradiated). 1.8M Ribose had 11% recovery of ultimate stress, 13% recovery of work to fracture, and 15% recovery of failure strain although none of these parameters were detected as significantly different from the Irradiated group. Similarly, 3M Ribose samples demonstrated recovery of these parameters but they were not significantly different from the Irradiated group. The most notable result was the effect of the High T Ribose treatment. There was a 47% recovery of work-to-fracture, 70% recovery of ultimate stress (p=0.004) and 43% recovery of failure strain (p=0.006). 1.8M Ribose and High T Ribose had the same solution concentration of ribose (1.8M) but different incubation temperatures (37° C. and 55° C., respectively). High T Ribose demonstrated a larger recovery of work-to-fracture (p=0.055 when compared to 1.8M Ribose), which suggests high temperature incubation increases the positive effect of the treatment on the mechanical properties.

Collagen Characterization.

Collagen Fragmentation and Crosslinks. The molecular weight distributions on SDS-PAGE gels showed that rat-tail tendon collagen and the non-irradiated control bone had four distinct bands: one for gamma (three alpha chains), beta (two alpha chains), and one for each of the two types of alpha chains. The gels showed less defined alpha bands, absence of the gamma and beta bands, and smearing in both the irradiated and ribose-treated groups. Irradiated bone collagen shows lower density alpha and beta chain banding and more smearing in the region lower than alpha bands. Similar to the Irradiated sample, the 1.8M Ribose samples also demonstrated less defined banding and smearing below the alpha chains. High T Ribose-treated bone collagen showed almost no alpha banding and an overall lower density stain in the lane than all other groups. In addition, the High T Ribose insoluble pellets were, on average, much denser than control and irradiated groups. Solubility was measured based on the difference between the starting weight and the weight of the freeze-dried pellet after the soluble compartment was removed by centrifugation. The High T Ribose samples were only 11% solubilized while the Non-Irradiated controls were 25% soluble and the Irradiated samples were 35% soluble. High T Ribose was significantly lower than Irradiated (p=0.007) but not statistically different from Non-Irradiated (probably due to high variance).

Figure 13:
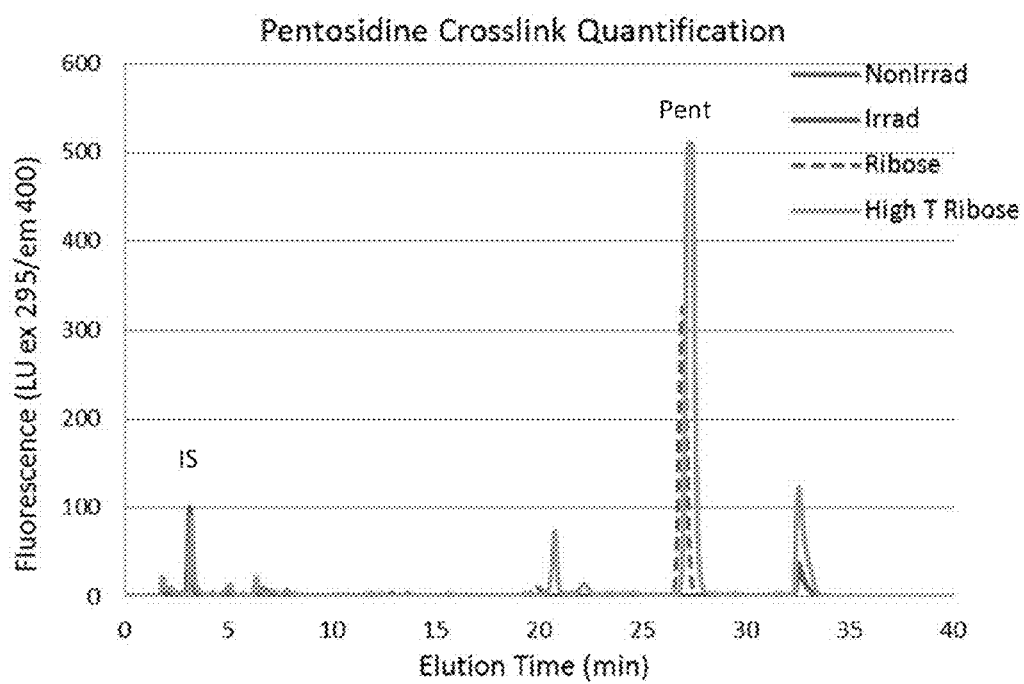
FIG. 13 shows representative chromatograms from HPLC. IS=internal standard Pent=Pentosidine. Ribose pre-treated samples show peaks corresponding to pentosidine and other glycation products.

Pentosidine was not detected in Non-Irradiated and Irradiated samples using HPLC. FIG. 13 shows representative HPLC elution profiles for one set of samples. There was a significant amount of pentosidine crosslinks measured in 1.8M Ribose treated samples and, on average, approximately 1.5 times that amount of pentosidine in the High T Ribose samples; however, a significant difference was not detected between the two ribose groups (p=0.342).

Thermal Stability

Irradiated bovine bone demonstrated significantly lower denaturation and peak temperatures in differential scanning calorimetry tests (p≤0.001 and p=0.001 respectively). When treated with 1.8M Ribose prior to irradiation, the demineralized bone collagen recovered 25% of denaturation and peak temperatures. The High T Ribose group demonstrated 70% recovery of onset and peak temperatures. DSC data on the control, irradiated, 1.8M Ribose, and High T Ribose groups showed no significant differences in measures of enthalpy.

Collagen Connectivity

Figure 14:
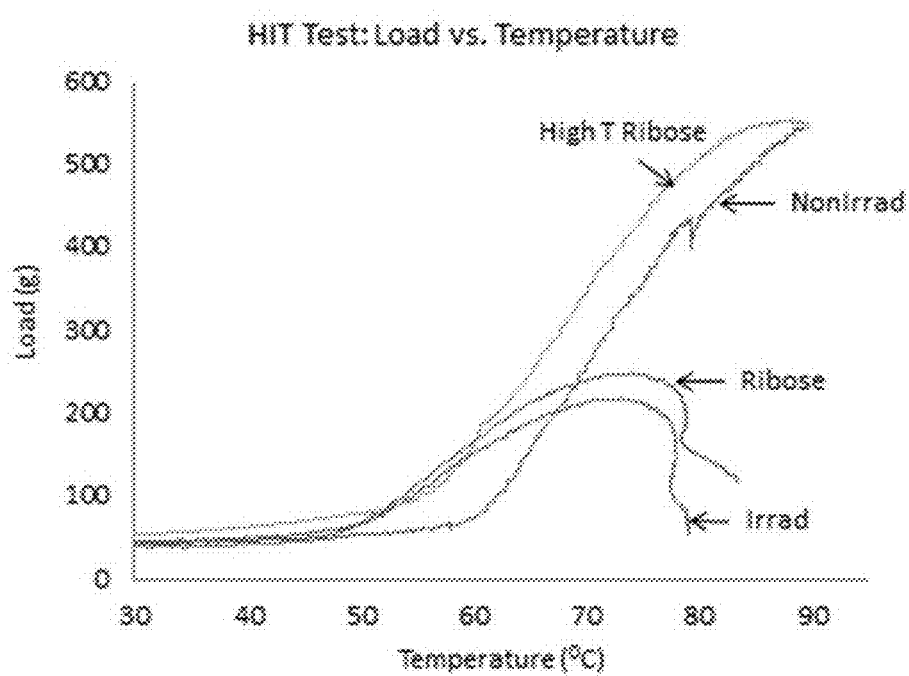
FIG. 14 shows representative curves for hydrothermal isometric tension for a matched set of demineralized bovine bone samples.

Bovine bone collagen subjected to irradiation had significantly different HIT curves when compared to normal bone. FIG. 14 shows typical load curves from HIT testing for one matched set of bone collagen specimens. Irradiated bone denaturation temperature and temperature at MIF were both reduced by ~20% (p≤0.001) while the slope of the curve and MIS were both reduced by ~47% (p≤0.001). The average $T_d$, slope at half max, TMIF and MIS for the 1.8M Ribose group were slightly higher than that of the Irradiated group, however the only significant difference detected was a 30% recovery of TMIF (p=0.016 compared to Irradiated). The High T Ribose group, on the other hand, recovered 74% of the slope, 90% of TMIF and 100% of Maximum Isometric Stress (p values indicate no significant difference detected between Control and High T Ribose).

In conclusion, this study shows that it is possible to recover toughness in irradiated bone using a pre-treatment with ribose. Incubating the bone in ribose solution at 55° C. recovered more work to fracture, ultimate stress, and fail strain than the same solution at 37° C. High temperature ribose treatment also had the effect of increasing measures of thermal stability and collagen connectivity (measured in DSC and HIT). The crosslinks created during treatment made the collagen more resistant to pepsin digestion. Overall, the results suggest that the degradation of collagen due to irradiation can be rescued with ribose treatment to increase the connectivity and stability of the collagen network, which in turn results in tougher bone.

Example 10

Comparing Ribose to Other Crosslinking Agents

The following methods were used in the study described in this Example:

Sample Preparation. A total of 10 tibias from steers (aged 2 years old) were used for this experiment. Samples were prepared as described in Example 9. Briefly, tibias were obtained immediately after slaughter and frozen (−20° C.) for 3-10 days. Then they were thawed, cleaned and cut into bone blocks. Two blocks from the distal portion of each tibia were used, allowing for 20 sets (see FIG. 4). Beam dimensions were 60 mm×4 mm×2 mm (l×w×t). After screening for any outlier samples with a non-destructive measurement of the modulus (see Example 9), there were at least seven (7) beams per set. Each beam was wrapped in saline-soaked gauze and stored frozen until further processing.

Treatment. Before treatment, all samples (aside from controls) were thawed at room temperature. All four agents (ribose, glucose, fructose, and ascorbate) were purchased in powder form from Sigma Aldrich. The agents were dissolved in PBS to a concentration of 1.8M and pH was adjusted to 7.4 with dilute HCL or NaOH as needed. Each set contained seven groups: Non-Irradiated, Irradiated, High T Irradiated, High T Ribose, High T Glucose, High T Fructose, and High T Ascorbate. The "High T" indicates the sample was incubated at 60° C. The agent was different for each group, with no agent in the High T Irradiated group. The beams were incubated in 45 mL of their respective solution. See Table 6 for a list of treatment conditions.

TABLE 6

Treatment Conditions prior to irradiation for Ribose, Glucose, Fructose and Ascorbate

| Group | Treatment | Incubation solution | Conditions: time/temp |
|---|---|---|---|
| NonIrrad | None | None | Frozen until testing |
| Irrad | Irradiation | PBS | 24 hrs/37° |
| High T Irrad | Irrad + high temp incubation | PBS | 24 hrs/60° |
| High T Ribose | Ribose + high temp incubation | PBS + 1.8M Ribose | 24 hrs/60° |
| High T Glucose | Glucose + high temp incubation | PBS + 1.8M Glucose | 24 hrs/60° |
| High T Fructose | Fructose + high temp incubation | PBS + 1.8M Fructose | 24 hrs/60° |
| High T Ascorbate | Ascorbate + high temp incubation | PBS + 1.8M Ascorbate | 24 hrs/60° |

Irradiation. Irradiation was performed with the help of Allograft Technologies at Mount Sinai Hospital in the same manner as described in Example 9. Briefly, all samples were packed in the center of a box surrounded with dry ice and sent to Steris Isomedix (Whitby, ON) where it was irradiated at ~30 kGy from a Cobalt-60 gamma irradiation source. The box was received within 24 hours of irradiation and samples were transferred into the freezer until testing.

Mechanical Testing. Three-point bending to failure was performed on all test samples to evaluate bulk mechanical properties. The method described in Example 9 was repeated for this set of samples. Briefly, bone beams were thawed at room temperature and polished by hand to a 1-um finish. Immediately after polishing, beams were placed in 15 mL PBS to soak for 4 hours (at room temperature) prior to testing in order to rehydrate the sample. Beams were placed into the machine (periosteal side down) and loaded at a constant crosshead displacement rate of 1.04 mm/min based on beam dimensions and strain rate of 0.005%/sec. The position of the crosshead, time, and load was recorded. The three-point bending tests were conducted using an Instron E1000 mechanical testing device with custom made fixtures. From the load and displacement data, a stress-strain curve was created from which various mechanical properties are calculated. The following parameters were determined from the stress-strain curve: elastic modulus (E), yield stress ($\sigma y$), yield strain ($\epsilon y$), ultimate stress ($\sigma u$), work to fracture (WFx), and failure strain ($\epsilon f$)

Dual Energy X-Ray Absorptiometry. Dual Energy X-Ray Absorptiometry (DEXA) was performed on one-half of each fractured sample after failure in three-point bending. Samples were scanned radiographically one at a time and in the same orientation to avoid differences based on placement in the device. The protocol described in Example 9 was repeated for these samples. The volumetric bone mineral density was calculated and averaged for each test group.

Collagen Characterization. Following mechanical testing, four of the groups were chosen for collagen characterization: Non-Irradiated controls, the Irradiated group, the High T Ribose treatment group and the High T Glucose treatment group.

Portions of the fractured beams located away from the fracture site were taken for collagen characterization. These portions of the bone beams were demineralized in EDTA for 3 weeks at room temperature, and then prepared for further procedures. The methods of collagen characterization were previously described in Example 9. They included investigating collagen fragmentation with SDS-PAGE, solubility to pepsin digestion, measuring thermal stability in differential scanning calorimetry, measuring thermomechanical properties with hydrothermal isometric tension testing, and quantifying pentosidine crosslinks with HPLC.

Statistical Analysis. The data in this Example are all presented as mean±standard deviation, with a p value of less than 0.05 considered statistically significant. Statistical analysis was performed using SPSS v18 (SPSS, Chicago, Ill., USA). One-way repeated measures ANOVA (RM ANOVA) was used to detect differences between the means of each group. Repeated measures ANOVA considers each sample within its matched set, which controls for inter-animal variance. A Holms-Sidak post-hoc analysis was used for multiple comparisons between groups when significance was detected using RM ANOVA. The adjusted p-values are reported when discussing a comparison between two groups.

The results of the study are described below.

Mechanical Properties

Three point bend tests to failure demonstrated the embrittlement of bone due to irradiation and recovery of toughness with the use of high temperature ribose pre-treatment. Controlling for the high temperature incubation had no protective effect; all measured parameters were nearly equal and no significant difference was detected between the Irradiated and High T Irradiated groups. These groups together are referred to herein as the "Irradiated" group. Table 7 (below) lists the results for modulus, yield stress, yield strain, ultimate stress, work to fracture, and failure strain. Modulus, yield stress, and bone mineral density (see Table 8 below) were not affected by irradiation or any of the treatments. Interestingly, the yield strain of the High T Ribose group was slightly higher than all other groups. It was significantly higher than the Irradiated, High T Glucose, and High T Fructose groups but not detectably different from Non-Irradiated controls.

The Irradiated group lost 15% ultimate stress, 56% work-to-fracture, and 43% failure strain ($p \leq 0.001$ for all three parameters when comparing to Non-Irradiated controls). The High T Ribose treatment was superior when compared to glucose, fructose and ascorbate in terms of recovery of mechanical properties. When comparing the High T Ribose group to the Irradiated group, there was a 57% recovery of work-to-fracture ($p<0.001$), a 50% recovery of fail strain ($p<0.001$), and 100% recovery of ultimate stress ($p=0.001$). High T Glucose resulted in some mild improvement of work to fracture, ultimate stress, and failure strain, although none of these parameters were detected as significantly different from the Irradiated group. High T Fructose treatment was also ineffective in recovery of mechanical properties; none of the calculated parameters were significantly different from the High T Glucose group. Ascorbate demonstrated protection (as expected because it is a free radical scavenger) however not as much recovery as the ribose treatment group (98% recovery of ultimate stress, p=0.001, and 33% recovery of work to fracture, p=0.004).

Collagen Characterization
Collagen Fragmentation and Crosslinks

Figure 15:
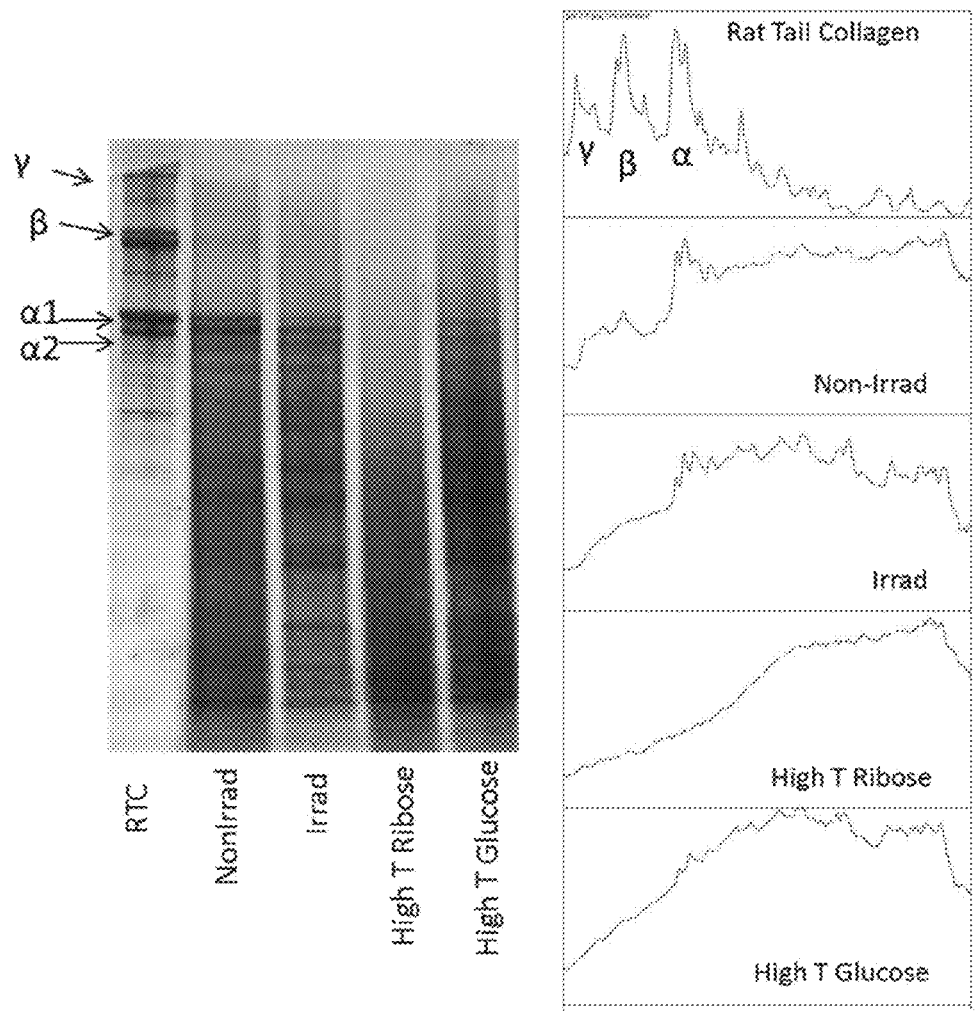
FIG. 15 shows a SDS-PAGE gel and stain density profile for one matched set of demineralized bone samples, comparing ribose and glucose pre-treatment to non-irradiated and irradiated controls. Ribose treated collagen was less susceptible to pepsin digestion and therefore not represented on the gels.

SDS-PAGE gels demonstrate the effects of irradiation and crosslinking treatments on the pepsin-soluble organic matrix after demineralization. The gamma, beta and alpha bands are less dense for irradiated samples and more smearing is apparent. High T Glucose samples had similar density profiles to the irradiated group, with a loss of gamma and beta bands, less dense alpha bands, and more smearing at low molecular weights. FIG. 15 shows a typical gel and stain density profile for one set of matched specimens. The High T Ribose treated samples show no evidence of banding (gamma, beta or alpha) and little staining in the lane at all, suggesting that perhaps the modified collagen remains in the pellet. To investigate this, some pellets were dried and weighed, then compared to the starting amount of bone powder. It was found that High T Ribose insoluble pellets were, on average, much denser than control, irradiated, and High T Glucose groups. On average, the High T Ribose samples were only 9% solubilized while the Non-Irradiated controls were 25% soluble, Irradiated samples were 31% soluble, and High T Glucose samples were 31% soluble. Significance, however, was only detected between High T Ribose and High T Glucose groups (p=0.043).

Pentosidine was not detected in Non-Irradiated, Irradiated, or High T Glucose samples using HPLC. The only group with pentosidine measured was the High T Ribose group, with an average of 45±4.7 mmol pentosidine per mol of collagen.

Thermal Stability

Figure 16:
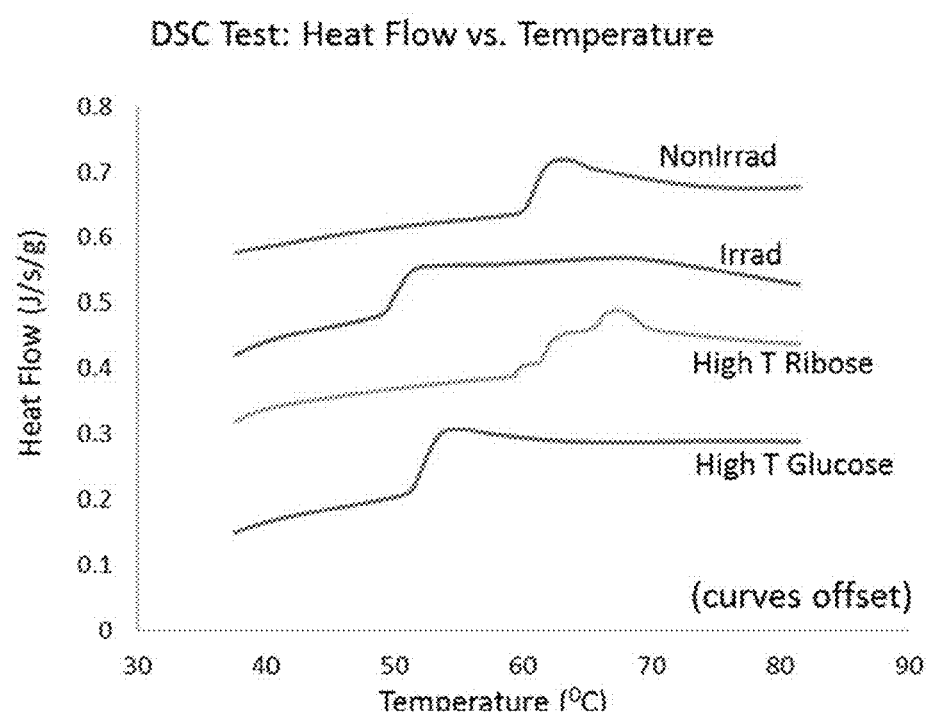
FIG. 16 shows representative curves from DSC for one set of matched specimens comparing ribose and glucose pre-treatments.

The irradiated bovine bone collagen showed a significant loss in denaturation and peak temperatures and an increase in enthalpy ($p \leq 0.001$ for all). The High T Ribose group demonstrated 100% recovery of onset and peak temperatures. In fact, denaturation temperature, peak temperature, enthalpy, and full width at half maximum (FWHM) were not significantly different between non-irradiated control and high temperature ribose treated groups. FIG. 16 shows example DSC curves for the non-irradiated, irradiated, and high temperature ribose groups from one matched set of specimens. The high temperature Glucose group demonstrated moderate recovery of $T_{ONSET}$ and FWHM (p=0.001, $p \leq 0.001$).

Collagen Connectivity

Figure 17:
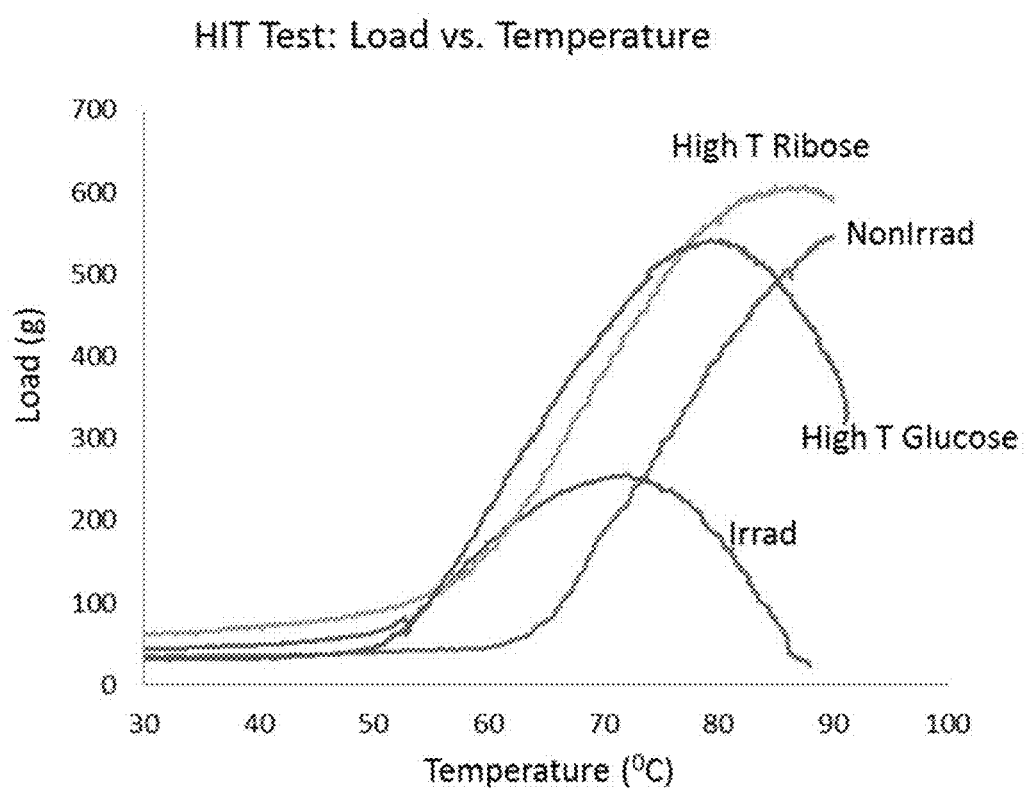
FIG. 17 shows representative curves from HIT for one set of matched specimens comparing ribose and glucose pre-treatments.

HIT testing revealed a loss of thermomechanical parameters for irradiated samples and recovery with the use of ribose and glucose pre-treatments. The temperature of denaturation and temperature at maximum isometric force were decreased by 10° C. and 20° C. ($p \leq 0.001$ for both) due to irradiation, which corresponds to a ~20% loss for both temperatures. On average, the irradiated samples showed a loss of 55% of the maximum isometric stress and 35% of the slope at half maximum when compared to non-irradiated controls ($p \leq 0.001$ for both). The High T Ribose group had 54% recovery of denaturation temperature, 93% recovery of temperature at MIF, 100% recovery of slope, and 100% recovery of Maximum Isometric Stress ($p \leq 0.001$ for all). FIG. 17 demonstrates the recovery of these thermomechanical measurements with example curves from one matched set of specimens. The High T Glucose group also demonstrated some recovery of the slope of the curve (72%, p=0.016), TMIF (39%, $p \leq 0.001$) and MIS (83%, $p \leq 0.001$) however the temperature of denaturation was not significantly different from the irradiated group.

High temperature incubation with ribose is more successful at recovering toughness than two other similar sugars: glucose and fructose. In comparison to glucose which was ineffective, ribose protects or restores 50% of the thermostability lost to irradiation.

Example 11

Fracture Testing of Irradiated and Ribose-Treated Bone

The following methods were used in the study:

Sample Preparation. Five tibias from steers (aged 2 years old) were used for this experiment. Samples were prepared in a similar manner to the method described in Example 9. Briefly, tibias were obtained immediately after slaughter and frozen (−20° C.) for 3-10 days. Then they were thawed, cleaned and cut into bone blocks. Two blocks from the distal portion of each tibia were used, allowing for ten sets but only nine were used. The blocks were machined into a set of three beams with dimensions of 60 mm×4 mm×4 mm (l×w×t) using a metallurgical saw (Buehler Isomet 1000) with a custom built fence followed by hand grinding and polishing. One beam was assigned to be a non-irradiated control, one beam was irradiated, and one beam was pre-treated with ribose and then irradiated. Each beam was wrapped in saline-soaked gauze and stored frozen until further processing.

Treatment and Irradiation. The samples (aside from control, which were left frozen until testing) were thawed at room temperature and placed in individual 50 mL tubes. D-Ribose in powdered form was dissolved in PBS to a concentration of 1.8M and pH was adjusted to 7.4 with dilute HCL or NaOH as needed. There were three groups in this experiment: Non-Irradiated, Irradiated, and High T Ribose. The Irradiated beams were incubated in 45 mL of PBS and the High T Ribose beams were incubated in 45 mL of 1.8M Ribose solution. Both the Irradiated samples and the High T Ribose samples were incubated in a water bath at 60° C. for 24 hours. After incubation they were removed from their solution, wrapped in saline soaked gauze, and frozen down for irradiation. Both the Irradiated and the High T Ribose group were irradiated at 30 kGy from a Cobalt-60 source at Steris Isomedix (Whitby, ON Canada).

Fracture Testing. Based on the ASTM fracture testing standards a single-edge notched beam (SENB) loaded in 3-point bending was used [15, 19, 36]. A machined notch was cut at mid-length into one face (periosteal to endosteal direction) of the sample with a 300 um-diameter diamond wire saw. The notch was further sharpened by hand by sliding a razor blade back and forth across the machined notch tip with 1 um diamond paste [19, 37]. The resulting machined notch and razor cut was a ~2 mm long singular crack, as shown in the inset SEM image in FIG. 18a. To encourage crack propagation down the center of the sample, side grooves with a depth of 0.5 mm were cut on the two side faces (lined up with the notch). Mode I loading was used, which requires that the direction of crack propagation is perpendicular to the direction of crack extension [38]. The beams were placed notch-side down into a 3-point bending jig, making sure that the notch was lined up with the center-line of the loading crosshead (6.35 mm diameter). The two supports (also 6.35 mm in diameter) were spaced 40 mm apart. FIG. 18(a) is a schematic representation of the testing set-up. FIG. 18b is an SEM image of the fracture surface with the notch, razor notch, and side-grooves labeled to illustrate the samples. Beams were loaded at a rate of 0.5 mm/min using an Instron E100 testing machine. Instron Bluehill data acquisition software was used to produce a load vs. displacement curve. The beams were loaded until there was a 10% drop in load, so that the point at maximum load was captured during the test but the samples were not fully fractured. Samples were mostly fractured (almost all the way through) at this point, so the two halves were separated carefully by hand by rapid snapping in order to expose the fracture surface for imaging with SEM (FIG. 18b). A load vs. displacement curve was created with the data from a test.

Imaging the Fracture Surface. The fracture surface was imaged using scanning electron microscopy (SEM) methods after failure in three-point bending. A portion of bone containing the fracture surface was removed from the rest of the sample with a Buehler Isomet 100 wafer saw, leaving at least 5 mm between the cut and the fracture surface to avoid damage. Methods previously published were used for preparation and imaging [39, 40, 41]. The fracture sample portions were soaked in 3% hydrogen peroxide for 48 hours, rinsed with distilled water, defatted in a 50:50 solution of methanol-chloroform (24 hours) then placed in 100% methanol for 1 hour and dried overnight in a desiccator. Samples were mounted on SEM stages such that the direction of propagation of the crack was parallel to the stage surface. They were then affixed to specimen stubs using conductive carbon cement (Leit-C Plast, Plano GMBH, Wetzlar, Germany). The mounted samples were sputter coated with gold for 125 s with a Denton Vacuum Desk II sputter coater (Moorestown, N.J., USA). Imaging was conducted with a scanning electron microscope (XL30 ESEM; Philips USA). Beam conditions were set at 20 kV accelerating voltage and a spot size of 4.

Calculating Fracture Toughness. Two important fracture toughness values calculated from test data were K and J. K is a parameter that describes the intensity of the triaxial stress at the crack tip, and is called the stress intensity factor. When the stresses and strains reach a certain value, the crack will start to propagate and K will have reached a critical value called $K_c$ [42]. $K_c$ is also known as the fracture toughness, an intrinsic material property independent of specimen geometry [38]. The following equation is used to calculate K from a load vs. displacement curve:

$$K = \frac{Pf\left(\frac{a}{W}\right)}{B\sqrt{W}}$$

Where P=load, a=crack length, W=width of the specimen, B=thickness of the specimen, and f(a/W) is a known function based on the geometry of the specimen. The load used in the calculation of $K_c$ must be the critical load that initiates crack propagation. If the load vs. displacement curve is considered, the non-linear portion of the curve from yield point to maximum load represents plastic deformation, including but not exclusively crack propagation. Thus, an estimation of the critical load, $P_Q$, is usually taken by using the intersection of the 95% secant line and the load-displacement curve [38]. After this point, there is stable crack propagation while the load and displacement continue to increase non-linearly. The maximum load marks instability point; the point after which the crack is unstable and fast fracture occurs. The beam is considered failed after the instability point is reached as there is no longer a building resistance to crack progression. In a material such as bone, which is not as homogeneous in microstructure as a metal, it is difficult to know an appropriate estimation of the critical load. For this study, fracture toughness was evaluated using $K_i$, or K calculated at the maximum load (instability point).

The second value to be calculated from load-displacement curves for the fracture tests is J. J is a mathematical representation of the energy release rate during crack propagation in a region of the material containing the crack tip. Under plane-strain conditions, meaning the following condition is satisfied:

$$B \geq 2.5\left(\frac{K_c}{\sigma_y}\right)^2$$

(where B is specimen thickness and $\sigma_y$ is yield strength):

$$J_{el} = G = K^2\left(\frac{1-v^2}{E}\right)$$

Where G is the elastic energy released per unit area of a new crack surface forming for an infinitesimal increment of crack extension [38], v is Poisson's ratio (estimated at 0.3) and E is Young's Modulus. This equation only accounts for the elastic energy release rate, so another term to account for the plastic energy release rate must be added:

$$J_{tot} = J_{el} + J_{pl} = \frac{K^2(1-v^2)}{E} + \frac{\eta_{pl} A_{pl}}{B b_0}$$

where $\eta_{pl} = 1.9$ and $b_0 = W - a_0$

Where $a_0$ is the initial crack length, B is the thickness of the specimen, W is the width and $A_{pl}$ is the area under the plastic portion of the load-displacement curve. If $J_i$ is evaluated at the maximum load ($P_{max}$) it will give the energy released at the point of instability. J and K were evaluated at $P_{max}$ to give a measure of each value at the instability point, $J_i$ and $K_i$ and because previous work has shown that irradiation greatly effects the crack growth between crack initiation and instability (R-curve) [19].

Estimating the Crack Length

Prior to the instability point at the maximum load, it is assumed that there may be some stable crack propagation. The surface appearance between stable and fast fracture is noticeably different [43]. Using SEM images of the fracture surface, it is possible to visually distinguish stable tearing from unstable tearing. Measurement of the stable tearing region on SEM images can give an estimate of the crack growth at the maximum load. This crack length can then be used in the calculation of $K_i$ (and subsequently in $J_i$) instead of just assuming the crack at maximum load is still the initial notch length.

Preliminary experiments were performed to explore this idea and more accurately estimate crack growth based on SEM images. Several specimens were loaded to $P_{max}$ and subsequently stained with alizarin red. The stain marked the edge of the crack, and when samples were then cut and imaged on the pre-fracture surface, it was possible to see the crack propagation leading up to instability (maximum load). The stain measurements from microscope images were comparable to separate measurements from SEM images using visual roughness as the measure of crack propagation. Information from this experiment confirmed that roughness of the stable tearing region is a good estimate of stable crack growth; however the specimens in this study were not stained for crack growth, only measured on SEM images with the preliminary results as a reference for what constitutes stable tearing.

The method for measuring crack propagation prior to instability is summarized below. An SEM image of the entire fracture surface of each specimen was taken and analyzed with ImageJ analysis software. Lines were normalized to the length bar scale on the image so that accurate measurements could be taken. Five vertical and five horizontal lines were drawn across the entire sample to get average measurements of the width and thickness. The depth of the side grooves, notch, and razor notch were also measured at five points. The edge of the stable tearing region was traced and five measurements across the fracture surface were taken. The average of these measurements was called $a_s$ for the stable crack propagation. The crack length was calculated as follows:

$$A_c = a_0 + a_r + a_s$$

Where $A_c$ is the crack length at instability, $a_0$ is the machined notch, $a_r$ is the razor notch and as is the stable crack propagation. $A_c$ was used in the calculation of Ki, specifically in the f(a/w) function. Using this estimation for the crack length and based on the load vs. displacement curves for each sample, $J_i$ and $K_i$ were calculated for Non-Irradiated, Irradiated, and High T Ribose groups.

Statistical Analysis.

The data in this Example are all presented as mean±standard deviation, with a p value of less than 0.05 considered statistically significant. Statistical analysis was performed using SPSS v18 (SPSS, Chicago, Ill., USA). One-way repeated measures ANOVA (RM ANOVA) was used to detect differences between the means of each group. Repeated measures ANOVA considers each sample within its matched set, which controls for inter-animal variance. A Holms-Sidak post-hoc analysis was used for multiple comparisons between groups when significance was detected using RM ANOVA. The adjusted p values are reported when discussing a comparison between two groups.

The results of the study are discussed below.

Irradiation had a negative effect on the fracture properties of bovine cortical bone. Both the J-integral at instability ($J_i$) and fracture toughness ($K_i$) were lowered due to irradiation. FIG. 19a shows example load vs. displacement curves for one matched set of fracture beams and FIG. 19b is a graph of the average values for $J_i$ for the three groups. There was a loss of 52% for $J_i$ (p=0.009) and a loss of 39% for $K_i$ (p=0.009) when comparing the Irradiated group to the Non-Irradiated controls. High T Ribose treatment resulted in a 30% recovery of $J_i$ (p=0.047) and 43% recovery of Ki although this was not detectably significant (p=0.102 for comparison of Irradiated to High T Ribose). There was no significant difference among any groups in respect to the average measurements for the stable tearing region found using SEM image analysis (RM ANOVA=0.211).

High temperature ribose pre-treatment demonstrates recovery of some of the fracture toughness of irradiated bovine cortical bone. This recovery may be due to the fact that irradiated bone collagen alone is weakened by cleavages of the peptide bond, and high temperature ribose treatment induces glyco-oxidation crosslinking that stabilizes the organic network.

Example 12

Irradiation-Sterilized Human Bone Allograft Toughened by Ribose Treatment

The following methods were used in the study described in this example.

This study used cortical bone from the diaphysis of five left human femurs. The donors were all male aged between 59 and 67 years. The bones were sourced through Mount Sinai Allograft Technologies after ethics approval from the hospital review board. From each diaphysial site (proximal, mid-shaft, distal), six matched beams (termed a set) were cut with a metallurgical saw and hand polished to a 1-um surface finish. The beams measured 2×4×50 mm (±10% max.). 15 sets were tested. One beam from each set was randomly assigned to one of six groups: non-irradiated controls (N; kept frozen until testing), irradiated controls (I), and four GOC pre-treatment groups. The Irradiated (I) and GOC groups were incubated in PBS at 60° C. for 24 hours. The GOC agent was ribose and the buffers contained increasing concentrations of ribose (GOC1=0.06M, GOC2=0.3M, GOC3=0.6M, and GOC4=1.2M). The Irradiated (I) and GOC groups were then packed on dry ice and irradiated at 34 kGy (±10%). All specimens were then thawed and rehydrated in PBS for four hours before mechanical testing. The beams were tested to failure in three-point bending following ASTM D790 as closely as possible using an Instron ElectroPuls E1000 testing machine. Flexural modulus (E), yield stress and strain ($\sigma_y$ and $\epsilon_y$), ultimate stress (US), failure strain ($\epsilon_f$) and work-of-fracture (Wfx) were determined from the test data. Repeated measures ANOVA with Holms-Sidak tests post-hoc were used to test between group differences at the 95% confidence level (p<0.05).

Figure 20:
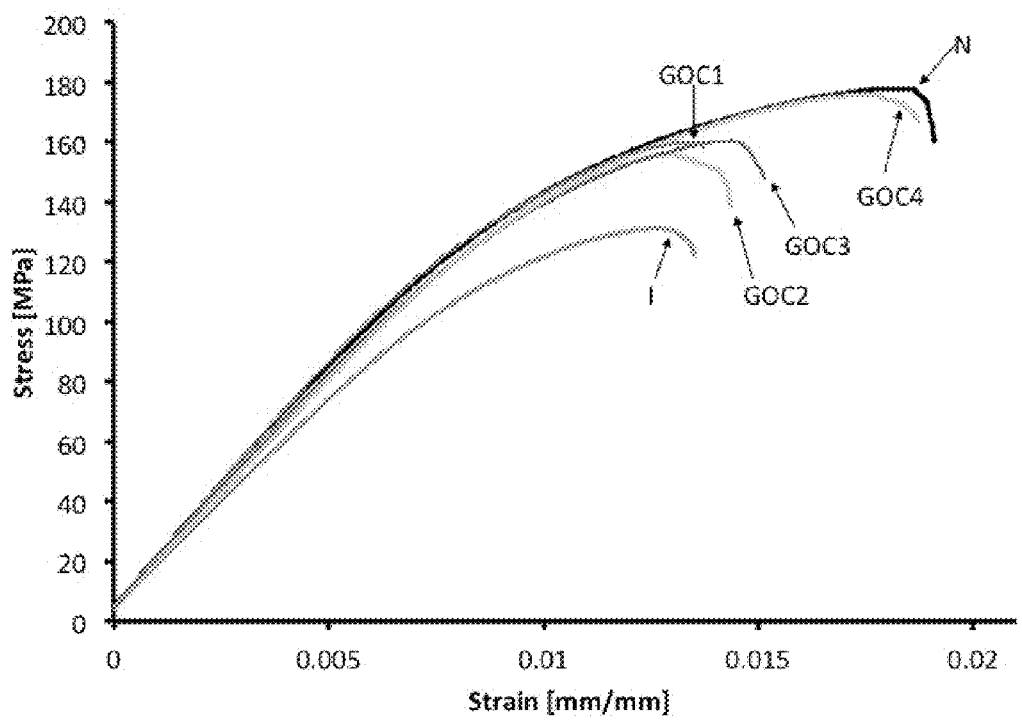
FIG. 20 shows representative stress-strain curves.

The results of the study are discussed below.

γ-irradiation sterilization at 34 kGY reduced the ultimate strength by 8% (p≤0.05), failure strain by 19% (p≤0.0001), and work-to-fracture by 29% (p≤0.0001) on average but did not detectably affect the flexural modulus (p=0.43) or yield point (p=0.22). GOC pre-treatment resulted in notable improvements of the affected measures in a concentration dependent manner. (See Table 9 below and FIG. 20). In the GOC4 group, US reached N levels (106%; p≤0.05 N vs. GOC4) and GOC recovered 60% of the strain at failure and 76% of the Wfx lost in I (both cases: p≤0.001 GOC4 vs. I; p≤0.05 GOC4 vs N). The effects of I and the GOC treatments were not detectably dependent upon diaphysial harvest site (p > 0.05).

The results of this study demonstrate that GOC pre-treatment before 34 kGy of γ-irradiation sterilization can be an effective means of improving the mechanical performance of irradiation-sterilized human bone. Therefore, various endogenous crosslinking agents might be applied to toughen irradiation-sterilized bone allograft. The increased work-of-fracture (toughness) is somewhat surprising because increased crosslinking in normal cortical bone is broadly thought to lead to reduced toughness. The modified collagen network is more connected and crosslinked than in γ-irradiated controls and the restored connectivity of the collagen may enable post-yield strain accommodation before failure. The human bone in this study was less affected by γ-irradiation than the bovine bone used in previous work (60% loss of Wfx) and GOC4 produced slightly better recovery of mechanical properties than in bovine bone.

This study demonstrates that the mechanical properties of irradiation-sterilized human bone can be improved using GOC pre-treatment followed by irradiation.

Example 13

Ribose Uptake into Human (Femur) Bone

The study was performed using the following method. Ribose incubation media was prepared prior to incubation at three concentrations, 0.6, 1.2, and 1.8 moles/L in PBS. 5 mL was used for bone incubation. Tritiated ribose, 1 mCi/mL and at 7.6 µg/mL, was diluted 1:10 which was then added to the incubation volume. The amount of tritiated ribose was kept at the same ratio to the "cold" ribose in all experiments. Usually 10 µL of diluted stock was added to the 0.6 M ribose solution, 20 µL to the 1.2 M ribose solution, and 30 µL to the 1.8 M ribose solution.

Previously shaped bone beams were thoroughly blotted and the wet weight was determined. The dimensions of the bone sample were also measured for subsequent volume calculation. The beams were placed into appropriate tubes, ribose incubation solution was added, tracer was added, mixed briefly, and an aliquot was withdrawn for counting (50 µL). The tubes were placed in a shaking water bath at the designated temperature for 23 hours.

Following incubation, bone beams were rinsed briefly with PBS twice and subsequently either washed with PBS for 24 hours at 60° C. or digested with 0.6 mL 50-70% nitric acid at 60° C., for 4 hours in a 20 mL glass scintillation vial fitted with an acid resistant cap insert. An aliquot from the rinsing solutions was taken as well for counting (50 µL). Following digestion, the vials were cooled to room temperature, 15 mL of Hionic Fluor (P-E) scintillation cocktail was added, gently mixed, allowed to stand for at least 2 hour before scintillation counting. Appropriate blanks were counted as well as quenching due to nitric acid was also accounted for.

Figure 21:
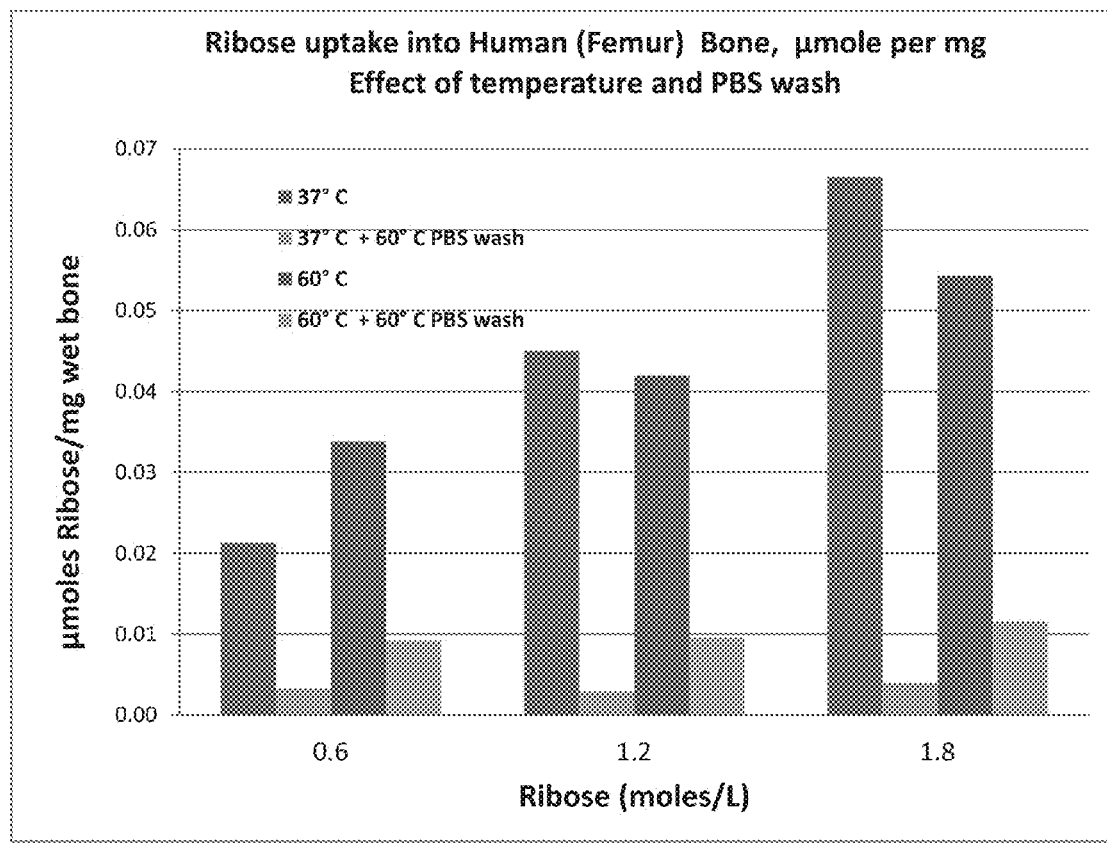
FIG. 21 shows a graph of the effect of temperature and phosphate buffered saline (PBS) wash on ribose uptake into human (femur) bone (μmole per mg).
Figure 22:
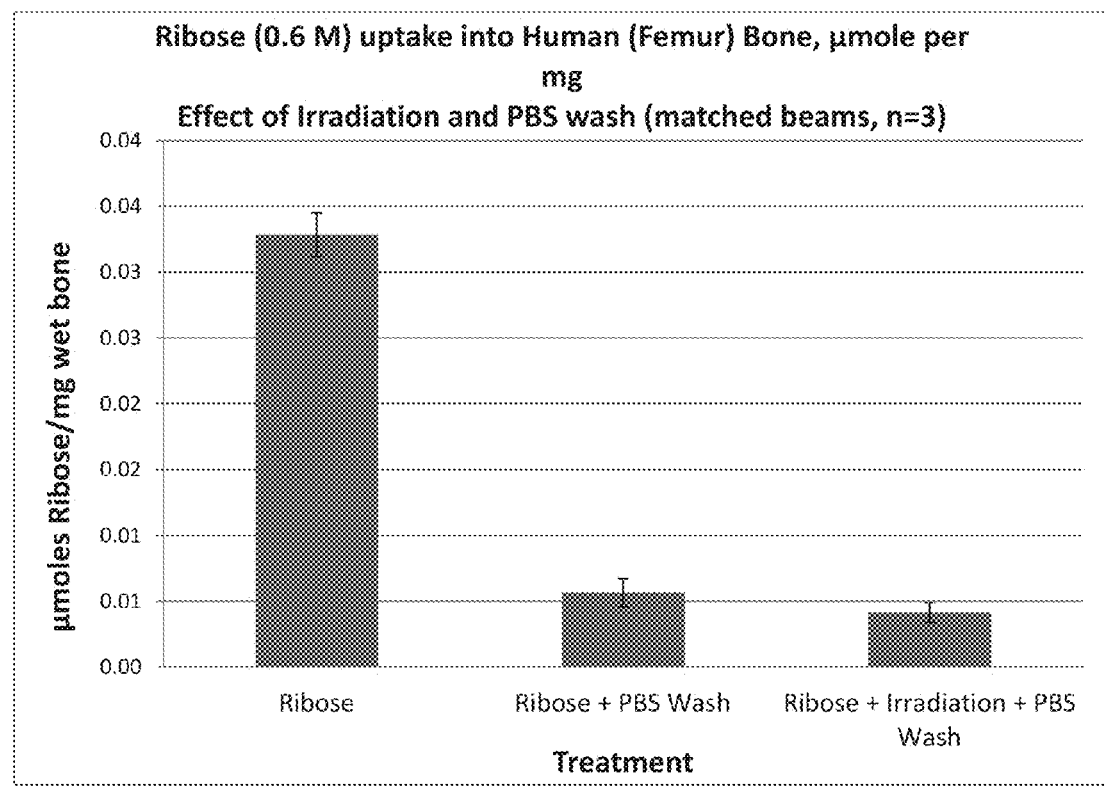
FIG. 22 shows the effect of irradiation and PBS wash (matched beams, n=3) on uptake of ribose (0.6M) into human (femur) bone (μmole per mg).

FIG. 21 shows the effect of temperature and PBS wash on ribose uptake into human (femur) bone, The absolute per mg of bone ribose incorporation was highest in the 1.8M bone and the uptake of ribose was about 0.01 µmole ribose/per mg wet bone at all concentrations at 60° C. PBS wash. FIG. 22 shows that irradiation does not appear to significantly effect the uptake of ribose into human (femur) bone.

Having illustrated and described the principles of the invention in preferred embodiments, it should be appreciated to those skilled in the art that the invention can be modified in arrangement and detail without departure from such principles. All modifications coming within the scope of the following claims are claimed.

All publications, patents and patent applications referred to herein, and priority application No. 61/717,321 filed Oct. 23, 2012, are incorporated by reference in their entirety to the same extent as if each individual publication, patent or patent application was specifically and individually indicated to be incorporated by reference in its entirety.

TABLE 4

Mechanical Properties of bovine bone beams tested in three-point bending. n = 14.

|  | E MPa | $\sigma_y$ | $\epsilon_y$ | $\sigma_u$ MPa | Wfx mJ/mm2 | $\epsilon_f$ |
|---|---|---|---|---|---|---|
| Non-Irrad | 18528 ± 1972 | 168.3 ± 21.9 | 0.875 ± 0.05 | 210.7 ± 24.9$^b$ | 6.40 ± 2.23$^{b,c}$ | 1.64 ± 0.45$^{b,c}$ |
| Irrad | 19765 ± 2260 | 161.7 ± 23.8 | 0.812 ± 0.09 | 168.2 ± 22.1$^{a,c}$ | 2.42 ± 0.83$^{a,c}$ | 0.896 ± 0.19$^{a,c}$ |
| Ribose (0.6M) | 19189 ± 2799 | 157.0 ± 17.14 | 0.816 ± 0.07$^{a,c}$ | 168.2 ± 22.1$^{a,c}$ | 2.74 ± 1.27$^{a,c}$ | 0.982 ± 0.29$^a$ |
| Ribose (1.8M) | 18952 ± 2610 | 160.0 ± 19.4 | 0.840 ± 0.08 | 178.3 ± 25.1$^{a,c*}$ | 2.92 ± 1.12$^{a,c*}$ | 1.01 ± 0.26$^{a,c}$ |
| Ribose (3.0M) | 17946 ± 1673 | 162.1 ± 22.6 | 0.850 ± 0.06 | 178.4 ± 28.2$^b$ | 3.10 ± 1.24$^{a,c*}$ | 1.06 ± 0.27$^{a,b,c*}$ |
| High T Ribose | 19855 ± 2257 | 170.9 ± 16.52 | 0.886 ± 0.05 | 180.1 ± 19.0$^b$ | 4.08 ± 1.37$^{c,b}$ | 1.23 ± 0.28$^{a,b}$ |
| RM-ANOVA | 0.123 | 0.279 | 0.003 | 0.002 | 0.001 | ≤0.001 |

E = flexural modulus,
$\sigma_y$ = yield stress,
$\epsilon_y$ = yield strain,
$\sigma_u$ = ultimate stress,
WFx = work to fracture,
$\epsilon_f$ = failure strain
[a]Statistically significant difference detected compared to Non-Irradiated (adjusted p < 0.05)
[b]Statistically significant difference detected compared to Irradiated (adjusted p < 0.05)
[c]Statistically significant difference detected compared to High T Ribose (adjusted p < 0.05)
x* indicates p values less than or equal to 0.10 but greater than 0.05 (for example c* means 0.05 < p value < 0.10 for comparison to High T Ribose)

TABLE 5

Bone mineral density of bovine beams measured with DEXA. n = 14

|  | Bone Mineral Density g/cm³ |
|---|---|
| Non-Irrad | 1.38 ± 0.07 |
| Irrad | 1.41 ± 0.11 |
| Ribose (0.6M) | 1.39 ± 0.07 |
| Ribose (1.8M) | 1.37 ± 0.06 |
| Ribose (3.0M) | 1.40 ± 0.10 |
| High T Ribose | 1.39 ± 0.07 |
| RM-ANOVA | 0.817 |

TABLE 7

Mechanical Properties from three-point bending comparing different agents

|  | E MPa | $\sigma_y$ MPa | $\epsilon_y$ | $\sigma_u$ MPa | Wfx mJ/mm2 | $\epsilon_f$ |
|---|---|---|---|---|---|---|
| Non-Irrad | 18842 ± 2126 | 168.1 ± 21.3 | 0.916 ± 0.035 | 207.54 ± 20.65$^b$ | 9.03 ± 2.03$^{b,c}$ | 2.21 ± 0.39$^{b,c}$ |
| Irrad | 18401 ± 1842 | 161.8 ± 16.3 | 0.905 ± 0.036$^c$ | 180.00 ± 17.44$^{a,c}$ | 3.76 ± 1.21$^{a,c}$ | 1.22 ± 0.26$^{a,c}$ |
| Irrad (high T) | 18009 ± 2121 | 158.2 ± 20.5 | 0.903 ± 0.034$^c$ | 176.43 ± 22.55$^{a,c}$ | 3.93 ± 1.48$^{a,c}$ | 1.27 ± 0.30$^{a,c}$ |
| High T Ribose | 19045 ± 2309 | 174.4 ± 22.0 | 0.942 ± 0.034$^b$ | 210.77 ± 24.97$^b$ | 6.84 ± 1.65$^{a,b}$ | 1.76 ± 0.34$^{a,b}$ |
| High T Glucose | 18137 ± 2516 | 162.5 ± 16.3 | 0.918 ± 0.032 | 189.50 ± 23.37 | 4.70 ± 1.12$^{a,c}$ | 1.41 ± 0.23$^{a,c}$ |

TABLE 7-continued

Mechanical Properties from three-point bending comparing different agents

| | E MPa | $\sigma_y$ MPa | $\epsilon_y$ | $\sigma_u$ MPa | Wfx mJ/mm2 | $\epsilon_f$ |
|---|---|---|---|---|---|---|
| High T Ascorbate | 19591 ± 2338 | 173.3 ± 22.3 | 0.908 ± 0.051 | 206.83 ± 20.99$^b$ | 5.61 ± 1.23$^{a,b}$ | 1.53 ± 0.30$^a$ |
| High T Fructose | 18484 ± 2164 | 162.7 ± 20.4 | 0.903 ± 0.032$^c$ | 190.30 ± 22.89$^a$ | 4.92 ± 1.57$^{a,c}$ | 1.44 ± 0.32$^{a,c}$ |
| RM-ANOVA | 0.187 | 0.207 | 0.004 | ≤0.001 | ≤0.001 | ≤0.001 |

E = flexural modulus,
$\sigma_y$ = yield stress,
$\epsilon_y$ = yield strain,
$\sigma_u$ = ultimate stress,
WFx = work to fracture,
$\epsilon_f$ = failure strain
$^a$Statistically significant difference detected compared to Non-Irradiated (adjusted p < 0.05)
$^b$Statistically significant difference detected compared to Irradiated (adjusted p < 0.05)
$^c$Statistically significant difference detected compared to High T Ribose (adjusted p < 0.05)
Irrad and Irrad (high T) were not significantly different from each other for any measured property
High T Glucose and High T Fructose were not significantly different from each other for any measured property

TABLE 8

Bone mineral density of bovine bone beams measured with DEXA

| | Bone Mineral Density g/cm³ |
|---|---|
| Non-Irrad | 1.40 ± 0.06 |
| Irrad | 1.37 ± 0.05 |
| Irrad (high T) | 1.39 ± 0.05 |
| High T Ribose | 1.39 ± 0.06 |
| High T Glucose | 1.36 ± 0.06 |
| RM-ANOVA | 0.134 |

TABLE 9

| Treatment Group | E (GPa) | $\sigma_y$ (MPa) | $\epsilon_y$ (%) | $\epsilon_f$ (%) | US (MPa) | Wfx (mJ/mm2) |
|---|---|---|---|---|---|---|
| N (non-irradiated) | 14.4 ± 1.6 | 132 ± 18 | 1.09 ± 0.09 | 1.80 ± 0.38 | 151 ± 25 | 4.22 ± 1.40 |
| I (irradiated control) | 14.6 ± 1.5 | 129 ± 18 | 1.05 ± 0.07 | 1.45 ± 0.19$^\#$ | 140 ± 22 | 2.99 ± 0.84$^\#$ |
| GOC1 (0.06M) | 14.4 ± 1.8 | 130 ± 20 | 1.06 ± 0.08 | 1.43 ± 0.19$^\#$ | 140 ± 23 | 2.90 ± 0.84$^\#$ |
| GOC2 (0.3M) | 14.6 ± 1.6 | 135 ± 27 | 1.09 ± 0.12 | 1.52 ± 0.27$^\#$ | 148 ± 32 | 3.35 ± 1.19$^\#$ |
| GOC3 (0.6M) | 14.2 ± 1.3 | 132 ± 16 | 1.10 ± 0.08 | 1.59 ± 0.23$^\#$ | 146 ± 18 | 3.39 ± 0.77$^\#$ |
| GOC4 (1.2M) | 15.2 ± 0.9 | 141 ± 18 | 1.09 ± 0.08 | 16.6 ± 0.17* | 160 ± 20* | 3.93 ± 0.79* |
| RM-ANOVA | p = 0.43 | p = 0.056 | p = 0.22 | p < 0.001 | p = 0.01 | p < 0.001 |

Data presented as mean ± standard deviation-n = 15
$^\#$indicates a statistically significant difference from N (non-irradiated controls)
*indicates a statistically significant difference from I (irradiated controls)

FULL CITATIONS FOR PUBLICATIONS (1) Musculoskeletal Allograft Tissue Safety. San Francisco, Calif.: American Academy of Orthopaedic Surgeons, 2010.
(2) Lakey J R, Mirbolooki M, Rogers C, Mohr J. Demand for human allograft tissue in Canada. Cell Tissue Bank 2007; 8(1):31-42.
(3) Mroz T E, Joyce M J, Steinmetz M P, Lieberman I H, Wang J C. Musculoskeletal allograft risks and recalls in the United States. J Am Acad Orthop Surg 2008; 16(10):559-565.
(4) Nguyen H, Morgan D A, Forwood M R. Sterilization of allograft bone: effects of gamma irradiation on allograft biology and biomechanics. Cell Tissue Bank 2007; 8(2): 93-105.
(5) Mankin H J, Friedlaender G E, Tomford W W. Massive Allograft Transplantation Following Tumor Resection. In: Friedlaender G E, Mankin H J, Goldberg V M, editors. Bone Grafts and Bone Graft Substitutes. Rosemont, Ill.: American Academy of Orthopaedic Surgeons, 2006: 39-47.
(6) Lietman S A, Tomford W W, Gebhardt M C, Springfield D S, Mankin H J. Complications of irradiated allografts in orthopaedic tumor surgery. Clin Orthop Relat Res 2000; (375):214-217.
(7) Thompson R C, Jr., Garg A, Clohisy D R, Cheng E Y. Fractures in large-segment allografts. Clin Orthop Relat Res 2000; (370):227-235.
(8) Akkus O, Belaney R M, Das P. Free radical scavenging alleviates the biomechanical impairment of gamma radiation sterilized bone tissue. J Orthop Res 2005; 23(4):838-845.
(9) Mitchell E J, Stawarz A M, Kayacan R, Rimnac C M. The effect of gamma radiation sterilization on the fatigue crack propagation resistance of human cortical bone. J Bone Joint Surg Am 2004; 86-A(12):2648-2657.
(10) Akkus O, Rimnac C M. Fracture resistance of gamma radiation sterilized cortical bone allografts. J Orthop Res 2001; 19(5):927-934.
(11) Akkus O, Belaney R M. Sterilization by gamma radiation impairs the tensile fatigue life of cortical bone by two orders of magnitude. J Orthop Res 2005; 23(5):1054-1058.
(12) Haimi S, Vienonen A, Hirn M, Pelto M, Virtanen V, Suuronen R. The effect of chemical cleansing procedures combined with peracetic acid-ethanol sterilization on biomechanical properties of cortical bone. Biologicals 2008; 36:99-104.

(13) Willett, T. L., Labow, R. S., & Lee, J. M. (2008). Mechanical overload decreases the thermal stability of collagen in an in vitro tensile overload tendon model. Journal of Orthopaedic Research, 26(12), 1605-1610.
(14) Willett, T. L., Labow, R. S., Aldous, I. G., Avery, N. C., & Lee, J. M. (2010). Changes in collagen with aging maintain molecular stability after overload: Evidence from an in vitro tendon model. *Journal of Biomechanical Engineering*, 132(3)
(15) Materials ASftTo. Standard test method for measurement of fracture toughness. ASTM, 2009.
(16) Bank R A, Beekman B, Verzijl N, de Roos J A, Sakkee A N, Tekoppele J M. Sensitive fluorimetric quantitation of pyridinium and pentosidine crosslinks in biological samples in a single high performance liquid chromatographic run. J. Chromatogr. B Biomed. Sci. Appl. 1997; 703:37.
(17) Levine R L, Wehr N, Williams J A, Stadtman E R, Shacter E. Determination of carbonyl groups in oxidized proteins. Methods Mol Biol 2000; 99:15.
(18) Yan J, Mecholsky J J, Jr., Clifton K B. How tough is bone? Application of elastic-plastic fracture mechanics to bone. Bone 2007; 40:479.
(19) Barth H D, Zimmermann E A, Schaible E, Tang S Y, Alliston T, Ritchie R O. Characterization of the effects of x-ray irradiation on the hierarchical structure and mechanical properties of human cortical bone. Biomaterials (2011) 32(34): 8892.
(20) Nalla R K, Kinney J H, Ritchie R O. Mechanistic fracture criteria for the failure of human cortical bone. Nat. Mater. 2003;2:164.
(21) Zimmermann E A, Schaible E, Bale H, Barth H D, Tang S Y, Reichert P, Busse B, Alliston T, Ager J W, 3rd, Ritchie R O. Age-related changes in the plasticity and toughness of human cortical bone at multiple length scales. Proc Natl Acad Sci USA (2011): 108:14416.
(22) Yan J, Clifton K B, Reep R L, Mecholsky J J, Jr. Application of fracture mechanics to failure in manatee rib bone. J Biomech Eng 2006; 128:281.
(23) Leng H, Wang X, Ross R D, Niebur G L, Roeder R K. Micro-computed tomography of fatigue microdamage in cortical bone using a barium sulfate contrast agent. J Mech Behav Biomed Mater 2008; 1:68.
(24) Landrigan M D, Li J, Turnbull T L, Burr D B, Niebur G L, Roeder R K. Contrast-enhanced microcomputed tomography of fatigue microdamage accumulation in human cortical bone. Bone; 48:443.
(25) Zioupos P, Currey J D, Hamer A J. The role of collagen in the declining mechanical properties of aging human cortical bone. J Biomed Mater Res 1999; 45:108.
(26) Bank R A, Krikken M, Beekman B, Stoop R, Maroudas A, Lafeber F P, Te Koppele J M. A simplified measurement of degraded collagen in tissues: application in healthy, fibrillated and osteoarthritic cartilage. Matrix Biol. 1997; 16:233.
(27) Willett T L, Labow R S, Avery N C, Lee J M. Increased proteolysis of collagen in an in vitro tensile overload tendon model. Ann. Biomed. Eng 2007; 35:1961.
(28) Wynnyckyj C, Willett T L, Omelon S, Wang J, Wang Z, Grynpas M D. Changes in bone fatigue resistance due to collagen degradation. J. Orthop. Res. (2011) 29(2): 197-203.
(29) Miles C A, Avery N C, Rodin V V, Bailey A J. The increase in denaturation temperature following cross-linking of collagen is caused by dehydration of the fibers. J. Mol. Biol. 2005; 346:551.
(30) Miles C A. Kinetics of collagen denaturation in mammalian lens capsules studied by differential scanning calorimetry. Int. J. Biol. Macromol. 1993; 15:265.
(31) Miles C A. Differential scanning calorimetry (DSC): protein structure probe useful for the study of damaged tendons. Equine Vet. J. 1994; 26:255.
(32) Miles C A, Wardale R J, Birch H L, Bailey A J. Differential scanning calorimetric studies of superficial digital flexor tendon degeneration in the horse. Equine Vet. J. 1994; 26:291.
(33) Kattaya S A, Akkus O, Slama J. Radioprotectant and radiosensitizer effects on sterility of gamma-irradiated bone. Clin. Orthop. Relat Res. 2008; 466:1796.
(34) An Y, Friedman R J. Animal Models of Bone Defect Repair. In: An Y, Friedman R J, editors. Animal Models in Orthopaedic Research. Boca Raton: CRC Press, 1999. p. 241.
(35) Callister W D. Diffusion. In: Callister W D, editor. Materials Science and Engineering: An Introduction. Toronto: John Whiley and Sons, 1994. p. 89.
(36) *Standard Test Methods for Linear-Elastic Plane-Strain Fracture Toughness KIC of Metallic Materials*, ASTM 399-90, 2010
(37) Yang, Q. D., Cox, B. N., Nalla, R. K., & Ritchie, R. O. (2006). Re-evaluating the toughness of human cortical bone. *Bone*, 38(6), 878-887.
(38) Hertzberg, Richard W. *Deformation and Fracture Mechanics of Engineering Materials*. Fourth ed. New Jersey: John Wiley and Sons, 1995
(39) Willett, T. L., Sutty, S., Gaspar, A., Avery, N., & Grynpas, M. (2013). In vitro non-enzymatic ribation reduces post-yield strain accommodation in cortical bone. *Bone*, 52(2), 611-622.
(40) Wise, L. M., Wang, Z., & Grynpas, M. D. (2007). The use of fractography to supplement analysis of bone mechanical properties in different strains of mice. *Bone*, 41(4), 620-630.
(41) Wynnyckyj, C., Wise-Milestone, L., Omelon, S., Wang, Z., & Grynpas, M. (2011). Fracture surface analysis to understand the failure mechanisms of collagen degraded bone. *Journal of Bone and Mineral Metabolism*, 29(3), 359-368.
(42) Zhu, X. & Joyce, J. A. (2012). Review of fracture toughness (G, K, J, CTOD, CTOA) testing and standardization. *Engineering Fracture Mechanics*, 85, 1-46.
(43) Yan, J., Clifton, K. B., Mecholsky Jr., J. J., & Reep, R. L. (2006). Fracture toughness of manatee rib and bovine femur using a chevron-notched beam test. *Journal of Biomechanics*, 39(6), 1066-1074.

What is claimed is:

1. A method of providing a bone allograft for use in a medical procedure comprising introducing a bone allograft in a container having disposed therein a composition comprising an irradiation activated agent, wherein the irradiation activated agent is in an amount effective to improve, or prevent or minimize loss of toughness, work-to-fracture, fracture toughness and/or fatigue strength on exposure of the bone allograft to radiation, wherein said irradiation activated agent is ribose, wherein the container comprises an outer impermeable layer, an inner layer for receiving a solution comprising a solute and the irradiation activated agent, and a sealable opening, wherein the inner layer is porous to the solute and optionally porous to the irradiation activated agent, and wherein the container comprises a self-sealing valve and the composition is introduced into the container through the self-sealing valve after the container is sealed.

2. A method for processing a bone allograft comprising (a) treating the bone allograft with an effective amount of an irradiation activated agent to improve, restore, protect, increase or prevent or minimize loss of, toughness, post-yield toughness, work-to-fracture, fracture toughness and/or fatigue strength on exposure of the bone allograft to radiation; (b) irradiating the bone allograft; and (c) optionally inactivating the agent, wherein the irradiation activated agent is 2-hydroxytetrahydropyran.

3. A method of providing a bone allograft for use in a medical procedure comprising introducing a bone allograft in a container having disposed therein a composition comprising an irradiation activated agent, wherein the irradiation activated agent is in an amount effective to improve, or prevent or minimize loss of toughness, work-to-fracture, fracture toughness and/or fatigue strength on exposure of the bone allograft to radiation, wherein the container comprises a self-sealing valve and the composition is introduced into the container through the self-sealing valve after the container is sealed, and wherein the container comprises an outer impermeable layer, an inner layer for receiving a solution comprising a solute and the irradiation activated agent, and a sealable opening, wherein the inner layer is porous to the solute and optionally porous to the irradiation activated agent.

\* \* \* \* \*